United States Patent [19]

Brenner

[11] Patent Number: 5,342,580
[45] Date of Patent: Aug. 30, 1994

[54] APPARATUS AND METHOD FOR MEASURING THE AMOUNT OF GAS ADSORBED ON OR DESORBED FROM A SOLID AND REACTIONS OF A GAS WITH A SOLID

[76] Inventor: Alan Brenner, 679 West Chester, Grosse Pointe Park, Mich. 48230

[21] Appl. No.: 510,505

[22] Filed: Apr. 17, 1990

[51] Int. Cl.$^5$ ............................................... G01N 7/02
[52] U.S. Cl. ...................... 422/92; 422/88; 436/34; 436/37; 436/147; 436/148; 73/73
[58] Field of Search .................. 422/92, 88, 83, 80; 436/34, 37, 147, 148, 159; 73/38, 73, 74, 149, 865.5

[56] References Cited

U.S. PATENT DOCUMENTS

| | | | |
|---|---|---|---|
| 2,753,246 | 7/1956 | Shields et al. | 436/37 |
| 3,059,478 | 10/1962 | Coggeshall et al. | 73/38 X |
| 3,211,006 | 10/1965 | Haley | 73/865.5 |
| 3,211,007 | 10/1965 | Atkins | 73/865.5 |
| 3,349,625 | 10/1967 | Benusa et al. | 73/865.5 |
| 3,585,861 | 6/1969 | Keng | 73/865.5 |
| 3,732,736 | 5/1973 | Glaude et al. | 73/865.5 |
| 3,850,040 | 11/1974 | Orr et al. | 73/865.5 |
| 4,489,593 | 12/1984 | Peters et al. | 73/865.5 X |
| 4,496,249 | 1/1985 | Lee et al. | 436/37 X |
| 4,515,751 | 5/1985 | Krieg | 422/88 X |
| 4,528,850 | 7/1985 | Witier | 73/865.5 |
| 4,566,326 | 1/1986 | Lowell | 73/865.5 |
| 4,626,412 | 12/1986 | Ebner et al. | 422/78 X |
| 4,762,010 | 8/1988 | Borghard et al. | 73/865.5 |
| 4,838,706 | 6/1989 | Coey et al. | 73/19.1 X |
| 4,856,320 | 8/1989 | Bose et al. | 73/30.01 |
| 4,865,996 | 9/1989 | Castleman et al. | 422/89 X |
| 4,967,591 | 11/1990 | Rouguerol et al. | 73/38 |
| 4,972,730 | 11/1990 | Camp et al. | 73/865.5 |
| 5,009,849 | 4/1991 | Ebner et al. | 436/34 X |
| 5,016,468 | 5/1991 | Jennings | 73/73 |
| 5,039,489 | 8/1991 | Gleaves et al. | 436/159 |
| 5,058,442 | 10/1991 | Yamanaka et al. | 73/865.5 |
| 5,109,716 | 5/1992 | Ito et al. | 73/865.5 |
| 5,157,960 | 10/1992 | Brehm et al. | 73/38 |

OTHER PUBLICATIONS

A. Jones, et al., Temperature–Programmed Reduction for Solid Materials Characterization, Marcel Dekker, Inc., vols. 23–25, pp. 68–79.

E. Petersen, et al., Catalyst Deactivation, Marcel Dekker, Inc., vols. 23–30, pp. 99–123.

H. Boer, et al., Automatic Apparatus for Catalyst Characterization by Temperature–Programmed Reduction/Desorption/Oxidation, Rev. Sci. Instrum. 53(3), Mar. 1982, pp. 349–361.

W. Blakely, et al., New Instrumentation and Techniques to Monitor Chemical Surface Reactions on Single Crystals Over A Wide Pressure Range ($10^{-8}$–$10^5$ Torr) in the Same Apparatus, J. Vac. Sci. Technol., vol. 13, No. 5, Sep./Oct. 1976 pp. 1091–1096.

The CDS 900 Bench–Scale Reaction System –Chemical Data Systems, Inc., 1987.

Series 4570 High Pressure/High Temperature Reactor-Stirred Reactors–Parr Instrument Co., pp. 43–47.

ChemiSorb 2800-Micromeritics (3 pages).

Autosorb–6–Automatic Volumetric Sorption Analyzer, Quantachrome Corp. (6 pages).

Catalyst Characterization –Computer-Controlled Temperature Programmed Systems–Altamira Instruments, Inc. (2 pages).

Primary Examiner—Robert J. Warden
Assistant Examiner—Roebrt Carpenter
Attorney, Agent, or Firm—Pollock, Vande Sande & Priddy

[57] ABSTRACT

An apparatus and method for measuring an amount of gas adsorbed on or desorbed from a solid and for analyzing and surveying reactions of a gas with a solid. Governing parameters include pressure, temperature and gas flow rate. The apparatus and method provide accurate measurement utilizing temperature programmed characterization and the volumetric method. The method is useful at both very high and very low pressures.

40 Claims, 9 Drawing Sheets

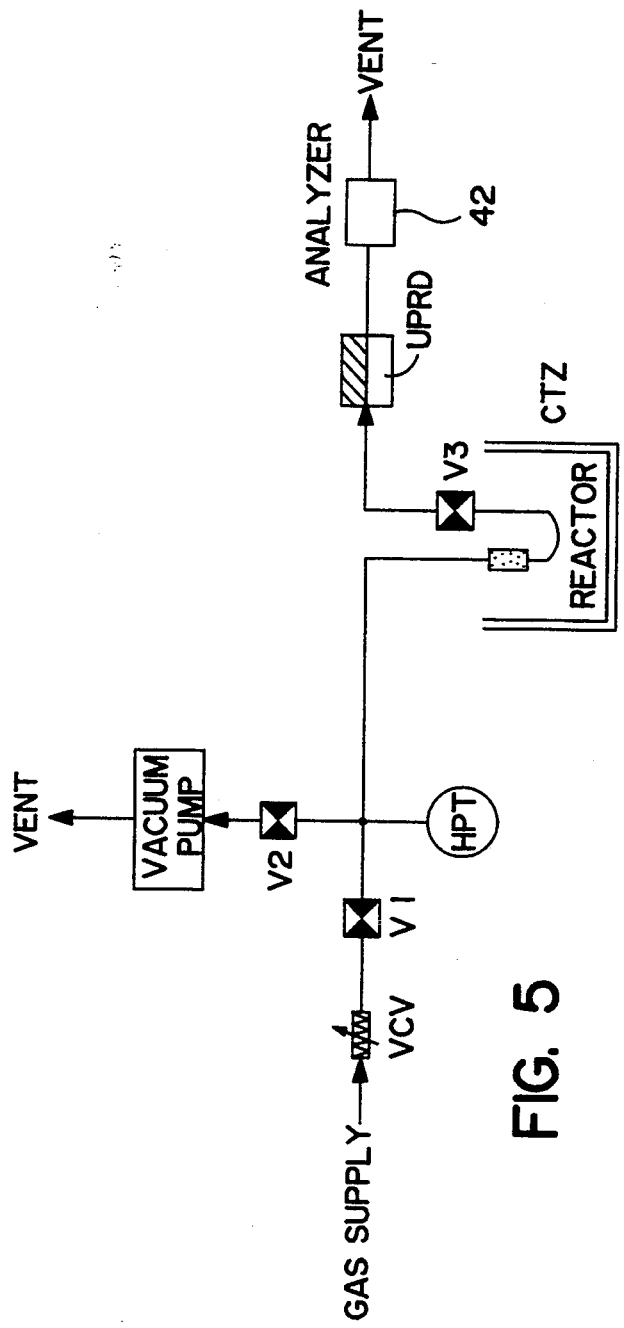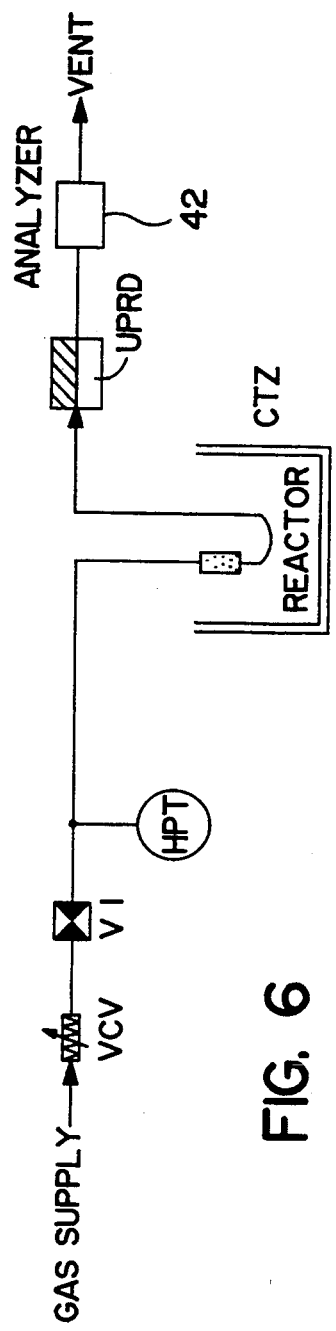
FIG. 5
FIG. 6

APPARATUS AND METHOD FOR MEASURING THE AMOUNT OF GAS ADSORBED ON OR DESORBED FROM A SOLID AND REACTIONS OF A GAS WITH A SOLID

The invention relates generally to an apparatus and method for measuring the amount of gas adsorbed on or desorbed from a solid. More particularly, the invention relates to an apparatus and method that will also provide a governing of the reactions of a gas with a solid by pressure and by temperature and by rate of flow in a broad range of those parameters. Most particularly, the invention provides an apparatus and method for very accurate measurement of the amount of gas adsorbed on or desorbed from a solid utilizing the volumetric method and means to govern the reaction of a gas with a solid at pressures ranging from substantially below one atmosphere to

BACKGROUND OF THE INVENTION

It is estimated that solid catalysts account for about 90% of manufactured chemicals, and thus are extremely important to the chemical industry. It is well known that the performance of a catalyst can be greatly altered by small changes in its properties. Therefore, measuring the rate and products of chemical reactions between gases and catalysts and the characterization of catalysts are important endeavors. The most common and important methods of characterizing a solid catalyst involve the measurement of the adsorption of a gas on and the desorption of a gas from a catalyst.

It is also important to characterize many other types of noncatalytic solids by measuring their interaction with a gas. One such method is to determine the pore structure of a solid by measuring the physical adsorption of a gas near its boiling point, this frequently being done with $N_2(g)$ near 77 K. For example, the weathering of concrete is influenced by it pore structure. Another example is to determine the strength or quantity of acidic sites on the surface of a solid polymer by measuring the adsorption of a base, such as $NH_3(g)$.

Reactivity measurements of a catalyst are almost always done at pressures at or above 1 atm, and it is common for such measurements to be done at pressures exceeding 10 atm. In contrast, some of the most important methods of characterizing a solid require measuring the adsorption and desorption of a gas at pressures substantially below 1 atm. One of the most accurate and important of these techniques is termed the volumetric method and requires high vacuum capability ($P<5\times10^{-5}$ torr, 760 torr=1 atm)

The measurement of reactivity typically involves exposing a catalyst to a reaction mixture and measuring the amount and type of products formed. This data yields the activity and product distribution of a catalyst at the given reaction conditions. It is normally desirable to control the rate of flow, temperature, and pressure of reactants in a reactor. By varying these parameters, information can also be obtained on the kinetics of a reaction including the rate constant, activation energy, and orders of the reaction.

Reactors operable at high pressure are made of metal. Since metal is strong, virtually all such reactorrs are rated at >1000 psia (14.7 psia=1 atm). Pressurized containers pose an explosion hazard. They are not combined with good vacuum capability and the volume of the reactor is usually not critical. Virtually all manufactured laboratory scale reactors usuable at high pressure have a volume in the range of 100 mL to 10 L.

A high pressure reaction system will have a high pressure gauge. Since such an apparatus is not designed for measuring the adsorption and desorption of a gas with a solid by the volumetric method, there is no need for also having a highly accurate low pressure gauge. The most accurate high pressure gauges have an accuracy of about 0.1% of full scale, but in the lower end of their range are much less accurate due to noise and drift. Therefore, such a gauge with a range of 1000 psia can measure a pressure to an accuracy of only about 53 torr. Assuming a very small reaction volume of 100 mL and a temperature of 20° C., this corresponds to an error in measuring the amount of gas present of 6.5 mL STP (STP=standard temperature and pressure). Due to the specific experimental steps required when measuring the adsorption and desorption of a gas with a solid by the volumetric method, the repeatability of a gauge is a more meaningful parameter than the accuracy of a gauge for calculating the accuracy of the amount of gas adsorbed on or desorbed from a solid. However, in some cases manufacturers do not give a repeatability specification. A rough value is for the repeatability to be 3-fold better than the accuracy. In this case, the previously described apparatus could be used to measure the amount of adsorption or desorption to an accuracy of about 2.2 mL. This is about 59-fold larger than is acceptable for the least accurate apparatus for measuring the amount of gas adsorbed on or desorbed from a solid utilizing the volumetric method.

The most common and important methods of measuring the interaction of a gas with a solid are to measure the adsorption and desorption of a gas with a solid. Especially important is the measurement of the amount of equilibrium physical or chemical adsorption or desorption of a gas with a solid as a function of pressure. Physical adsorption and desorption data enable the determination of important properties of a solid including its surface area and pore structure. Chemical adsorption and desorption data enable the determination of a variety of properties of a solid including the dispersion and average crystallite size of a supported metal, the number and strength of acidic and basic sites on a solid, the energetics of adsorption and desorption, and the number of catalytically active sites on a solid.

There are two main techniques of doing these measurements: the volumetric method and the flowing gas technique The volumetric method is easily the most accurate, informative, and widely applicable. For both methods there is virtually no limit on the specific (per gram) or total surface area of a solid sample. In particular, samples of specifice surface area from 0.01 to 1500 $m^2/g$ can be used.

In the volumetric method a dose of gas at an accurately known pressure and temperature is expanded from a dosing volume of accurately known size into a reactor containing a sample at constant temperature. Gas laws enable the calculation of the quantity of gas contained in the dosing volume. Initially He gas is used as the dosing gas, and this enables an accurate determination of the pressure drop caused by the expansion of a nonadsorbing gas. The reactor and dosing volume are then evacuated and the process repeated with an adsorbate. By accurately measuring the gas pressure before and after the valve is opened, it is possible to accurately calculate the amount of gas which is adsorbed on the solid. A permutation of this technique enables the desorption of a gas to be measured.

Since the calculations of gas adsorbed or desorbed involve gas laws, the accuracy and sensitivity of the data are inversely proportional to the sum of the volumes of the reactor plus dosing region plus pressure transducer. For this reason this total volume is kept small, a typical value being 30 mL.

The data are highly sensitive to leaks and outgassing of the apparatus and any residual contamination. Especially if the solid being investigated is a catalyst, the sensitivity to such spurious effects can be great, with the exposure to 0.001 mL STP of contaminant over the lifetime of the measurement (roughly 1 h) sufficient to alter the results in some cases. A scratch or other inadvertent channel to the atmosphere 0.5 cm long by only $2 \times 10^{-4}$ cm diameter is sufficient to cause such a leak. Therefore, great attention to details of construction and operation of such an apparatus is required. Standard methods of vacuum technology can result in a system with low leak and outgassing. Residual gases are quickly removed by evacuation. When the measurements are of physical adsorption or desorption, it is common practice to use a mechanical vacuum pump capable of achieving a vacuum of about $10^{-3}$ torr. If chemical adsorption or desorption is being measured, which is generally much smaller in amount and much more sensitive to contamination and leaks, it is common practice to use a high vacuum pump capable of achieving a vacuum of at least $10^{-5}$ torr.

Due to the unreactive surface which they provide, glass vessels are often used for reactions in the low pressure regime. Evacuated glass containers pose an implosion hazard.

The measurement of adsorption or desorption of a gas with a solid by the volumetric technique also requires a very accurate pressure gauge. The accuracy of the results strongly depend on the accuracy of the pressure gauge. The large majority of measurements are made in the pressure range of 0 to 300 torr, but sometimes pressures near 1 atm are used. Therefore, it is common practice to utilize a pressure gauge which reads to about 1000 torr. A mediocre gauge for this type of apparatus and pressure range has an accuracy of about 0.3% of full scale. Gauges of this and much higher accuracy which have full scale ranges of 1 to 1000 torr are readily available. The mediocre gauge can measure a pressure with an accuracy of 3 torr. Assuming a typical reaction volume of 30 mL for an apparatus designed for such measurements and a temperature of 20° C., this corresponds to an error in measuring the amount of gas present of 0.11 mL STP. As noted previously, this results in an error for measuring the amount of adsorption or desorption of about 0.04 mL STP. Apparatus which are of substantially lower accuracy are not operable to meaningfully measure the adsorption or desorption of a gas with a solid by the volumetric technique.

Numerous devices are available to control the reaction of gases with solids at pressures $\geq 1$ atm. One prior art device is the model CDS 900 bench scale reactor system made by Chemical Data Systems, a division of Autoclave Engineers, Inc. of Oxford, Pennsylvania. This apparatus is capable of monitoring catalytic reactions at pressures between 1 atm and 1500 psia. A sample can be heated at temperatures up to 540° C. Heating and cooling of the reactor are relatively slow. Parr Instrument Company of Moline, Illinois, manufactures a model 4570 stirred reactor which will operate from 1 atm to 5000 psia. A sample can be heated at temperatures up to 500° C. Heating and cooling of this reactor are also relatively slow. Parr and Autoclave Engineers manufacture a number of other devices which operate in the high pressure regime, but none which operate in the low pressure regime.

It is sometimes desirable to evacuate a high pressure reactor. This is done with a mechanical pump. A mechanical pump can reduce the pressure to about 0.01 torr in a reasonable amount of time which results in the removal of 99.999% of the gas in the reactor. Since such apparatus are not designed for measuring the adsorption and desorption of a gas with a solid by the volumetric method, there is no need for also having a high vacuum pump and all of its required gauges, flow paths, and peripheral valves. Whereas high pressure reaction equipment is necessarily robust, high vacuum equipment is relatively easily damaged. Furthermore, as will be described in a following section, due to the fact that the tubing in the high pressure system is of small diameter but large diameter tubing is required for useful operation of a high vacuum pump, even attaching such a pump would not result in achieving high vacuum in an acceptable amount of time. Therefore, the aforementioned prior art can not be readily modified to operate at high vacuum.

Reactors used at high pressures are constructed of metal which has a high thermal conductivity. Therefore, they are also not suitable for immersion in liquid $N_2$ which is the standard temperature for most measurements of the physical adsorption or desorption of a gas with a solid.

Consequently, there is no prior art apparatus which is capable of operating in the high pressure regime in a manner suitable for running chemical reactions and which can also operate in the low pressure regime in a manner suitable for accurately measuring the adsorption or desorption of a gas with a solid by the volumetric method.

Numerous devices are available to measure the adsorption and desorption of gases with solids at low and ambient pressure regimes by the volumetric method. A prior art device is the model Chemisorb 2800 device made by Micromeritics of Norcross, Ga. This apparatus is capable of monitoring the chemical adsorption of a gas on a solid catalyst in the pressure range of about 1000 to $10^{-3}$ torr. Pretreatment of a sample can be done at pressures down to $10^{-5}$ torr and temperatures up to 750° C. Thorough evacuation of a solid sample is a standard procedure when pretreating a solid prior to measuring the adsorption of a gas on it, and several additional evacuations are also required as part of the adsorption measurement. Evacuation of a solid contained in a sample holder and mounted on a Chemisorb 2800 is relatively slow. In practice, it is found that it takes about 30 to 60 min to reduce the pressure from 1 atm to $1 \times 10^{-5}$ torr. Exclusive of the evacuation time, a measurement of the chemisorption of a gas on a solid takes about 1 h. Thus, the time for the evacuations substantially increases the total time of an adsorption measurement. Heating rates of the Chemisorb 2800 are about 10° C./min, and it takes about 1 h to cool a reactor from 650° to 35° C.

Quantachrome of Syosett, N.Y., manufactures a model Autosorb 6 which measures the physical adsorption of $N_2$ gas at $-196°$ C. on a solid in the pressure range of about 0.1 torr to 1 atm. Pretreatment of a sample can be done at pressures down to $10^{-3}$ torr and temperatures up to 450° C. Micromeritics and Quantachrome manufacture a number of other devices which operate at low or ambient pressure for the purpose of monitoring the adsorption or desorption of a gas with a solid, but none which operate at high pressure.

U.S. Pat. No. 4,489,593 issued in 1984 to Pieters and assigned to Omicron Technology Corporation of Berkeley Heights, N.J., is entitled "METHOD AND APPARATUS FOR DETERMINING THE AMOUNT OF GAS ADSORBED OR DESORBED FROM A SOLID". The apparatus claimed therein is exemplified by the model 100 manufactured by Omicron. This apparatus measures the physical adsorption and desorption of a gas with a solid in the pressure range of about 1000 to $4 \times 10^{-4}$ torr by measuring the pressure differential in a dynamic and volumetric manner as gas is continuously added to or withdrawn from the sample chamber. The apparatus can achieve an ultimate vacuum of about $10^{-7}$ torr and a solid sample can be heated to about 450° C. This and other apparatus for measuring the adsorption and desorption of gases which are manufactured by Omicron are inoperable at pressures above 1000 torr.

Catalysts are often affected by exposure to air and require in situ pretreatments which often take as long as obtaining the desired experimental measurement. A sample can not be introduced to any of the aforementioned prior art apparatus without first exposing the sample to air. Therefore, if a sample is pretreated on one apparatus, there is both the inefficiency of transferring the sample to the second apparatus as well as having to repeat the pretreatment on the second apparatus.

There is no prior art apparatus which provides for the accurate measurement of the amount of gas adsorbed on or desorbed from a solid by the volumetric method and which can also function in the high pressure regime in a manner suitable for controlling chemical reactions.

Accordingly, it is an object of this invention to provide an apparatus which can accurately measure the reaction, adsorption, and desorption of a gas with a solid in a pressure range extending from well below to well above 1 atm. It is in particular an object of this invention to provide the apparatus with means to accurately measure the amount of gas adsorbed on or desorbed from a solid by the volumetric method. It is further an object of this invention to provide relatively fast rates of evacuation and a very low ultimate vacuum. In particular, it is an object of this invention to extend the low pressure range to $10^{-9}$ torr. It is an object of this invention that chemical reactions performed at high pressures and adsorption or desorption measurements performed at low pressures can be done on a single sample without removing the sample from the apparatus or exposing it to air.

A second and less accurate and less widely applicable technique of measuring the equilibrium amount of adsorption or desorption of a gas with a solid is defined as the flowing gas technique. This method consists of passing a constant flow of gas over a solid sample at essentially constant temperature while a detector more or less continuously analyzes some parameter of the effluent gas in order to measure the disappearance of a component of the gas flow due to adsorption on the sample or the appearance of a component in the gas flow due to desorption from the sample. More particularly, the analyzer detects the adsorption or desorption of a gas with the solid by more or less continuously monitoring the concentration of the reactant gas which is contained in a large excess of an unreactive carrier gas. The detector is commonly a thermal conductivity detector and the gas flow is almost always at ambient pressure. Some of the analyzers, including a thermal conductivity detector, are capable of operating at high pressures.

For example, a flow of 10% $N_2$ in He can be flowed over a solid sample at 20° C. Adsorption of $N_2$ at this temperature will be negligible and thus establishes a baseline for the detector. A cryogenic flask containing liquid $N_2$ is then put around the reactor. The adsorption of the gaseous $N_2$ is then monitored at 77K. This information can be used to calculate the surface area of a solid.

Some important properties of solids, such as the pore size distribution, can not be measured by this technique. This technique is also very limited in its ability to measure the amount of adsorption or desorption of a gas with a solid as a function of pressure. The main advantage of this technique is that the requisite apparatus is cheaper than for the volumetric technique, primarily because vacuum capability is not required. A permutation of this technique enables similar measurements of the desorption of a gas.

A generalization of the flowing gas technique involves changing the temperature of the sample at a known and normally constant rate while the analysis is being performed. This method is commonly referred to and is here defined as temperature programmed characterization (TPC). These measurements include temperature programmed desorption, reaction, decomposition, reduction, and oxidation. In virtually all cases the temperature increases during the measurement. The most important of these techniques is temperature programmed desorption, which necessarily requires that the temperature increase with time. This method provides kinetic information on the nature of the desorption process. The reverse method, temperature programmed adsorption, requires that the temperature be reduced in a carefully controlled manner which is relatively difficult and this method is very rarely reported in the scientific literature. This method can provide thermodynamic information on the nature of the adsorption process. None of the aforementioned prior art apparatus can perform temperature programmed adsorption.

The flowing gas technique requires a small system volume. The amount of undesirable band spreading of an adsorption or desorption peak in the gas stream is proportional to the volume of the reactor plus analyzer plus interconnecting tubing. Also, the response time of the technique increases linearly with this volume. For these reasons this volume is kept small, a typical value being about 10 mL.

Control of leaks, outgassing, and contaminants is much harder in this type of system since vacuum technology is not normally used. In contrast to the case for systems which use the volumetric technique, no manufacturer of this type of equipment gives specifications for the degree of leak tightness or contamination of the apparatus. It is a common misconception that a leak from the atmosphere into an apparatus will not occur if the apparatus is at a pressure of ambient or above. In fact, inboard leaks through a sufficiently narrow channel occur at a rate independent of the internal pressure of an apparatus. As previously described, such leaks can seriously effect a measurement.

In order to remove residual gas when the composition of the flowing gas is changed, it is necessary to purge the flow lines for an extended time. The time necessary to purge the lines increases as their volume increases and is also substantially increased by any volume within the lines which is not directly swept by the flowing gas. Virtually all values contain some nonswept volume, and this is especially true of packless valves which are the valves having the lowest leak rate. A time of about 1 h is required to thoroughly purge a system of small volume. This time period, termed the equilibration time, substantially increases the analysis time fsince the additional time to perform TPC is about 1 h.

None of the prior art devices previously described can properly perform TPC. For example, the CDS 900 does not provide the necessary analyzer and flow path for the reactor effluent and the large volume in the apparatus would distort the data and diminish the sensitivity and accuracy of a measurement. The Chemisorb 2800 also does not have a suitable gas analyzer.

An example of an apparatus capable of TPC measurements is the AMI-1 manufactured by Altamira Instruments, Inc. of Pittsburgh, Pa. The AMI-1 uses a thermal conductivity detector. The AMI-1 is designed to flow gas through a glass reactor in the flow range of 5 to 80 mL/min at a maximum temperature of 1100° C. and maximum heating rate of 40° C./min. The apparatus can not do TPC at subambient temperatures. The temperature of a solid sample can not be cooled at a known and constant rate so temperature programmed adsorption can not be performed with this apparatus. No specification is given for the rate of cooling of the furnace. The AMI-1 is only operable near ambient pressure and has neither vacuum nor high pressure capability.

In a recent review of experimental methods and instrumentation for TPC (Alan Jones and Brian D. McNicol, Temperature-Programmed Reduction for Solid Materials Characterization, M. Dekker, Inc., New York, 1986, chapter 3) it is stated that all current apparatus only operate at ambient or subambient pressures, and the use of such a device at high pressure would be of great technical value. Another recent description of some TPC apparatus is provided by Menon (Catalyst Deactivation, Marcel Dekker, Inc. 1988, p. 99). H. Boer et. al. (Rev. Sci. Instrum. 53, 349 (1982)) described one of the very few apparatus which can perform temperature controlled adsorption. None of the apparatus described can also measure the amount of gas adsorbed on or desorbed from a solid sample by the volumetric method.

The AMI-1 also has a gas sampling valve which can be used to pass pulses of a gas over a sample. This enables some measurements to be made of the amount of adsorption of gas by using a thermal conductivity detector to monitor the disappearance of gas from the pulse. However, in most cases the data obtained is less accurate than obtained with the volumetric method and the amount of equilibrium adsorption as a function of pressure can not be measured.

It is therefore a further object of the present invention to provide an apparatus which can perform TPC as well as measure the reaction, adsorption, and desorption of a gas with a solid at low, ambient, and high pressures including the ability to accurately measure the amount of gas adsorbed on or desorbed from a solid utilizing the volumetric method. Another object of the present invention is to greatly lower the equilibration time for TPC. Still another object of the present invention is to provide controlled cooling of a solid sample in such a manner that measurements of temperature programmed adsorption can be performed.

The prior art devices previously described which only operate in the pressure regime at or below about 1 atm have no means of controlling or measuring high pressure gases and the introduction of high pressure gases could easily damage components of the apparatus and possibly cause the apparatus to explode.

Accordingly, it is also an object of this invention to provide an apparatus for measuring the reaction, adsorption, and desorption of a gas with a solid at low and high pressures with protection of the low pressure components of the apparatus from damage when the apparatus contains a gas at high pressure and to provide for safe operation of said apparatus.

Menon (Catalyst Deactivation, Marcel Dekker, Inc. 1988, p. 101) describes the use of a mass spectrometer as the detector for temperature programmed desorption done by the flowing gas technique. A mass spectrometer operates at pressures $<10^{-5}$ torr, so it is contained in its own evacuated chamber of large volume. It is necessary to reduce the pressure of the portion of the effluent gas which is analyzed. A common method is to pass some of the gas through a molecular leak so that a very small amount of gas is bled into the evacuated chamber containing the mass spectrometer probe. This pressure reduction leads to a very large degradation of the signal to noise ratio in the mass spectrometer. For this reason some companies, such as UTI of Milpitas, Calif., manufacture an unconventional ion source, called a closed ion source, for the mass spectrometer which reduces but does not eliminate this problem.

Another method of performing temperature programmed desorption is to monitor the gas phase as the sample is evacuated after being exposed to an adsorbate. This method is here defined as temperature programmed desorption by direct evacuation. In particular, in this method a solid sample contained in an evacuable chamber is exposed to an adsorbate. The temperature of the sample is then raised at a known rate while the sample chamber is evacuated and an analyzer contained in an evacuated chamber continuously measures some parameter of the desorbed gas. The standard practice is to place both the solid sample and a mass spectrometer probe within the same large evacuated chamber. This method has much higher sensitivity than the flowing gas technique. However, only samples of relatively low surface area can be used and the apparatus normally only operate at high vacuum. This conventional method of performing temperature programmed desorption differes substantially from the method of the present invention in which the mass spectrometer probe is place in a separate evacuated chamber and the reactor is in air and is isolatable from the evacuated chamber by means of a shutoff valve.

In 1976 Blakely et. al. (J. Vac. Sci. Technol. volume 13, number 5, 109) described an ultra high vacuum apparatus which was modified to enable monitoring chemical surface reactions on single crystals over a wide pressure range. The apparatus incorporates analysis methods used in surface science including low energy electron diffraction, Auger electron spectroscopy, and mass spectrometry which are contained in a large ultra high vacuum chamber. The vacuum chamber was modified to enable a removable cup to be placed over the sample and the cup has gas lines, essentially forming a reactor. The reactor is contained within the large chamber which is at high vacuum. It is alleged that reactions can be done at pressures up to 100 atm within the cup. This arrangement is very cumbersome and is very limited in application. This distinguishes from the present invention, wherein the reactor is exposed to air and is isolatable from vacuum by a shutoff valve.

This device differs in many other ways from the present invention. The apparatus of Blakely only enables reactions to be done on single crystals using samples having a total surface area of about $1 \times 10^{-4} m^2$, corresponding to a specific surface area of $<0.01 m^2/g$. However, very few materials are single crystals, no practical catalyst uses single crystals, and all practical catalysts have much higher surface area. A typical value for a practical catalyst is $100 m^2/g$, so that a typical sample size of 1 g has a surface area $10^6$-fold higher than capable of being used in the Blakely apparatus. This apparatus has no sample holder to contain a powdered or pelleted sample, whereas almost all catalysts are of this type. The present invention has no restriction on the specific surface area of a sample and the sample chamber accommodates powdered and pelleted samples. No means is described for cooling a sample in the Blakely apparatus, so neither the surface area nor pore structure of a solid can be determined with this apparatus. The apparatus also has no dosing volume, so measurements can not be made of the amount of adsorption and desorption of a gas with the sample using the volumetric technique. Reactions can only be done in the circulating mode, whereas the present invention enables the more useful methods of the flow mode and batch mode as well as being operable in the circulating mode.

Accordingly, it is also an object of the present invention to provide a means of using a mass spectrometer to monitor the desorption of a gas from a solid of specific surface area from about 0.01 to 1500 $m^2/g$ in such a manner as to substantially increase the sensitivity of the measurement over the conventional value and achieve this improvement without the complication and expense of a closed ion source.

It is evident that a wide temperature range is encountered in the variety of measurements which are used to measure the reaction, adsorption, or desorption of gases with a solid. For example, measurements of the surface area and pore structure of solids are routinely done at $-196°$ C. Many chemical reactions and pretreatments of solids require high temperatures. For example, gamma alumina, which is an important catalyst support, undergoes substantial changes in its physical properties at temperatures near $1200°$ C.

With the aforementioned prior art, much time is lost by the relatively slow heating of furnaces to reaction temperature and the subsequent slow cooling of a furnace. The slow thermal response of a furnace is exacerbated if it must be capable of operation at very high temperatures. This is because safety considerations generally limit the temperature which the outer surface of a furnace can have, and this in turn requires additional insulation of a furnace. Larger furnaces in term have a larger heat capacity which slows heating and cooling. For example, ATS of Butler, Pa., manufacturers a model 3110 tube furnace with a temperature rating of $1200°$ C. This furnace is alleged to heat and cool very fast. The minimum O.D. recommended for the furnace is 8″. The heating rate of this furnace is about $40°$ C./min. Cooling is found to be quite slow below about $100°$ C. Similar furnaces are available with temperature ratings up to $1650°$ C. A typical time for pretreating a catalyst or affecting a chemical reaction of a gas with a solid at a temperature of $1200°$ C. is $<1$ h. Therefore, the time spent heating and cooling substantially increases the total time of the process.

Therefore, it is an object of this invention to provide an apparatus which can measure the reaction, adsorption, or desorption of a gas with a solid over a very wide range of temperature, including temperatures up to $1650°$ C., and which can heat and cool a reactor extremely quickly. It is also an object of this invention to provide means for a furnace and insulated container containing a cryogenic fluid to be very rapidly removed and installed on an apparatus so the temperature of a sample can be changed over the range of from $-196°$ to $1650°$ C. in only a few minutes.

Glass reactors are widely used for chemical reactions. Compared to reactors constructed of metal, glass has the advantages of being transparent, more chemically inert, and capable of withstanding higher temperatures. For example, stainless steel is the most common metal used to construct chemical reactors. The temperature limit for stainless steel for such an application is approximately $500°$ C., and in some cases deleterious reactions with chemical feedstocks occur at much lower temperature. Reactors made of fused quartz are usable to above $1200°$ C. Ceramics, such as fused alumina, can be used to construct reactors of substantially higher temperature rating.

The major disadvantages of glass and ceramics are they can not withstand high pressures and are fragile. When a glass reactor is attached to a metal reaction system, there are two main places in which breakage occurs. The first is at the ends of the reactor where fittings couple the reactor to the rest of the apparatus. Breakage occurs due to the glass being crushed by the compressive forces of the fitting. In many cases the reactor has a U shape, with a gaseous or liquid fluid entering one arm and exiting from the other. In this case, a second weak spot is the bottom of the U. Breakage occurs here due to torque transmitted to the reactor when the fittings are tightened. Although various manufacturers claim their fittings to be free of torque, when used with a glass U shaped reactor experience shows that breakage is common.

One method to prevent the first type of breakage is to use a glass to metal seal. Such seals are commercially available, are leak tight, and provide a metal termination for a reactor. In some cases a soft elastomer, such as VITON rubber, is used to make the seal so only modest compressive forces are required. While this reduces breakage of the first type, it does not eliminate it and elastomers are less chemically inert and adsorb and desorb gases more than metal or glass. This lowers the accuracy of measurements of the adsorption or desorption of a gas with a solid made by the volumetric technique.

Breakage of the second type can be reduced by constructing a glass bridge between the two arms of the reactor. However, excessive torque will now cause the reactor to break at the position of the bridge. Micromeritics Instrument Corporation of Norcross, Ga., avoids this problem by using a reactor which has only a single point of attachment to the rest of the system, thereby eliminating the U shape. This is achieved by using concentric tubing to provide means of both entrance and exit for gas. However, this design suffers from the need to have elastomeric O-ring seals within the reactor with the aforementioned undesirable features and in addition the design results in a much lower gas conductance than a design which does not use concentric tubes and this will substantially slow evacuation of the reactor.

It is therefore an object of this invention to provide a glass reactor which is free of elastomers, has a high conductance for evacuation, can be attached to an apparatus for measuring the reaction, adsorption, or desorption of a gas with a solid in a highly leak free manner, and which is highly resistant to breakage.

It is seen that devices for the control and measurement of the flow of gases at high and low pressures are widely used in apparatus which measure the reaction, adsorption, and desorption of gases with solids. Further, control and measurement of the gas environment is crucial to the operation of such apparatus and frequently limits the operating range of such apparatus. In describing the nature of existing devices, it is useful to divide pressure into three regimes: the low pressure regime consists of pressures below 1 atm, the high pressure regime consists of pressures above 30 psia, and the ambient pressure regime refers to the range bounded by 1 atm and 30 psia.

To achieve pressures much below 1 atm requires the use of a vacuum pump. A rotary pump may be used to achieve a pressure of about $10^{-3}$ torr, but lower pressures require both a rotary pump and a second pump of the high vacuum type, such as a diffusion pump or turbomolecular pump. Such pumps can achieve an ultimate vacuum of about $1 \times 10^{-9}$ torr, but can not operate above about 0.3 torr. Further, exposure of such pumps to pressures above about 0.3 torr can often damage the pump. For this reason, the attainment of high vacuum requires a rotary vacuum pump, a high vacuum pump, multiple valves, evacuation paths, and a pressure gauge operable near 0.3 torr so that the pressure can be reduced below about 0.3 torr before the high vacuum pump is used to evacuate the chamber.

The measurement of pressure in the low pressure regime is also a specialized field, with various types of gauges being needed to cover the range from $10^{-9}$ torr to 1 atm. None of the gauges useful for measuring very low pressures can operate near 1 atm, and many of them will be damaged by exposure to a pressure above $10^{-2}$ torr. Gauges useful at very low pressures almost invariably operate on an ionization principle and are relatively inaccurate. A separate gauge, usually a themocouple or Pirani gauge, is necessary to measure pressure in the range of about 0.001 to 10 torr.

The design of a vacuum system requires great attention to the materials used with respect to such criteria as their mechanical integrity under vacuum, minimization of the adsorption of gases onto the walls of the system, outgassing of components, diffusion of gases through walls, extreme leak tightness of seals, inner diameter (I.D.) of tubing, and pumping speed. Speed of evacuation is an especially important and difficult design parameter.

At pressures below about 0.1 torr the mass transport of a gas occurs by molecular flow in most containers. The ability of a tube to transport gas is often measured by its conductance. In the regime of molecular flow, the conductance, C, of a tube is independent of the pressure and is approximately given by $$C = C_m = 12.2 d^3/l \text{ L/s}$$

where d is the diameter and l is the length of the tube in cm. A tube which is 30 cm long will have a conductance of 87 L/s if its I.D. is 6 cm, and will have a conductance of $7 \times 10^{-6}$ L/s if its I.D. is 0.025 cm. At a pressure of $1 \times 10^{-6}$ torr, the former conductance corresponds to a rate of mass transport of a gas with a specific gravity of 1 (such as $N_2$) of $1 \times 10^{-4}$ mL STP/s, an extremely low value.

The critical affect of the I.D. of tubing on the performance of vacuum systems can also be demonstrated by the following example. The time to evacuate a volume of size V from an initial pressure of $P_i$ to a final pressure of $P_f$ if the volume is connected to a vacuum pump of pumping speed S by tubing of conductance C is $$t = (V/S_{eff}) \ln(P_i/P_f)$$

where the effective pumping speed, $S_{eff}$, is given by $$1/S_{eff} = 1/S + 1/C.$$

A pumping speed of about 100 L/s is typical for a high vacuum pump. Consider a volume of 0.1 L which is to have its pressure reduced from $7.6 \times 10^{-2}$ to $7.6 \times 10^{-4}$ torr (a factor of 100) and is connected to a vacuum pump of speed 100 L/s by a 30 cm length of tubing with an I.D. of either 6 cm or 0.05 cm. Tubing with an I.D. of 6 cm yields an evacuation time of 0.01 s, and tubing with an I.D. of 0.05 cm yields an evacuation time of $9 \times 10^3$ s.

In order to achieve reasonable rates of evacuation, it is therefore common for the I.D. of tubing in an apparatus capable of achieving a good vacuum to be at least several centimeters. Tubing used in vacuum systems is generally of wide bore and relatively thin wall thickness.

The proper selection of valves is also critical in an apparatus which functions at low pressure. In order to obtain pressures $< 10^{-7}$ torr it is generally necessary to use packless valves which are also free of lubricant and are tested to be very leak tight. The orifice of the valves must be of substantial size to avoid restricting the pumping speed of a system. Packless valves are more expensive and available in much less variety than packed valves.

The criteria for the design of apparatus which transport gas at only modest vacuum and at high pressure are quite different. At pressures above about 1 torr the mass transport of a gas often occurs by laminar flow. In this pressure regime, the conductance of a tube depends on pressure and is approximately given by $$C = C_l = 183 \, d^4 P/l \text{ L/s}$$

where d is the diameter and l is the length of the tube in centimeters and P is the average pressure in the tube in torr. A tube which is 30 cm long and has an average P of 760 torr will have a conductance of $6 \times 10^6$ L/s if its I.D. is 6 cm, and will have a conductance of $2 \times 10^{-3}$ L/s if its I.D. is 0.025 cm. A tube which is 30 cm long, has an I.D. of 0.025 cm, and has an inlet pressure of 3 atm and an outlet pressure of 1 atm is found to transport $N_2$ gas at a rate of 410 mL STP/s. Typical flow rates of gases in laboratory scale gas and reaction systems operating at $\geq 1$ atm are 0.1 to 30 mL STP/s. Therefore, mass transport is not a problem in this pressure regime.

An additional illustration is provided by the previous example of evacuation time except in this instance the pressure is to be reduced from 760 to 7.6 torr (a factor of 100) and the speed of the vacuum pump is 1 L/s, a value typical of rotary pumps. Tubing with an I.D. of 6 cm yields an evacuation time of 0.5 s, and tubing with an I.D. of 0.05 cm yields an evacuation time of 33 s. Further, the reduction of pressure from >1 atm to 1 atm is rapidly accomplished by venting a chamber and without the use of a vacuum pump.

It is therefore seen that the mass transport of gases in the high pressure regime occurs by a different process and at much higher rates than in the low pressure regime. Further, the ability to transport a given amount of gas is rarely a design concern in the high pressure regime and tubing of relatively small I.D. can be used. Tubing used in pressurized systems is generally of small bore and relatively thick wall thickness.

The maintenance and control of high pressure in a chamber through which gas flows also requires some type of regulating device to isolate the high pressure zone from atmospheric pressure. This is commonly done with a device such as back pressure regulator. It has also been noted that the type of gauge used for measuring high pressure differs from that operable at very low pressure.

Valve selection for pressurized systems is normally straightforward. High pressure valves are usually not rigorously tested for leak tightness under vacuum and possess lubricants. Orifice size is not a concern for the flow rates used in laboratory scale apparatus. For example, a valve designed to attach to tubing of outer diameter 0.25" will pass $1.5 \times 10^4$ mL STP/s of air with a pressure drop of only 10 psi across the valve. As the pressure rating of an apparatus increases, the selection of valves and components suitable for high vacuum performance rapidly decreases and the price and complexity of the apparatus increases. For these reasons, there are breaks in the design of such an apparatus at pressures of about 200, 1000, and 3500 psia. In particular, at pressures above 3500 psi only packed valves are readily available.

The introduction of more than one pressurized gas into a common volume can cause back flow of one gas into the supply line of another gas. To prevent this hazardous situation, apparatus operating at high pressure contain check valves. This hazardous situation is not of concern in machines operating below 1 atm and a check valve would prevent the evacuation of any volume on the upstream side of the check valve.

It is also common practice to include filters in the flow lines of pressurized apparatus. The filters trap particulate matter which can damage valves and other components. Such particulates can be transported by the flow of gases and liquids in a pressurized machine, but are not readily transported in a vacuum. Conventional sintered disc metal filters, which have a surface area of about 0.04 sq. in. when placed inside of $\frac{1}{4}$" O.D. tubing, do not significantly impede the flow of gas in pressured devices. Filters are not normally used in tubing to be evacuated and will normally greatly reduce the speed of evacuation. Filters of large surface area, typically >0.2 sq. in., are also widely available and are used for passing extremely high flows of fluids. Such a filter is contained in a chamber having a volume of about 13 mL. The use of two such filters to protect against particulate matter in a reactor would degrade the accuracy of a measurement by the volumetric technique of the amount of gas adsorbed or desorbed with a solid by a factor of two. It is seen that filters of especially exotic design are required in such apparatus in order not to seriously degrade both the pumping speed and the sensitivity of the apparatus.

It is sometimes necessary to measure the amount of gas adsorbed on or desorbed from a solid sample of significant size, such as a catalyst pellet of 1 cm diameter. This requires a large I.D. of the tubing in the reactor. As previously described, extra volume decreases the accuracy of such measurements utilizing the volumetric method.

It is therefore also an object of this invention to provide a means for lowering the dead volume of a reactor used for such measurements.

It is also sometimes desirable to measure the amount of adsorption at a low equilibrium pressure utilizing the volumetric method. This is easy with manually operated valves, since the operator can throttle the gas flow. However, in a computer controlled apparatus using remotely actuated valves this becomes difficult. A typical time for a remotely controlled packless valve to close is about 0.5 s. If the dosing volume is initially evacuated, then opening a valve to a gas source will cause a gas burst before the valve can be closed. Further, in a well designed apparatus evacuation at pressures about 0.1 torr will be so fast that the pressure also can not be readily set by reducing a higher pressure. An error in setting the pressure of 1 torr at a pressure of 100 torr is inconsequential for adsorption measurements, but is not acceptable if the pressure of the gas in the dosing volume is to be less than about 10 torr.

Accordingly, it is also an object of this invention to provide improved means for setting low pressures in the dosing volume used for measuring the adsorption of a gas on a solid by the volumetric method.

Commercial apparatus for measuring chemical reactions or the adsorption or desorption of a gas with a solid are normally contained in a suitable enclosure. If an apparatus is to be highly multifunctional in its application, then it is likely that occassional changes in the fluid paths will be necessary. In addition, it is desirable to have easy access to the interior components for maintenance and troubleshooting. An enclosure makes such access difficult. A common practice when dealing with apparatus handling gas flows is to have various inlet and outlet valves mounted on the wall of the enclosure. However, this requires that the fittings be disconnected if it is necessary to remove the wall to get access to the interior. Especially if the apparatus is to operate at high vacuum or high pressure, it is most desirable to absolutely minimize the number of fittings which must be manipulated. This presents a challenging design problem.

It is therefore also an object of this invention to provide an apparatus which operates at high and low pressures and which has unusually facile means of being modified and maintained.

It is seen that pressures below 0.001 torr are necessary for important and common methods of characterization of surfaces which involve measuring the adsorption and desorption of a gas with a solid. However, almost all reactions done for the purpose of obtaining a product or evaluating the reactivity of a solid are done at pressures $\geq 1$ atm. It has been also shown that the physical laws governing the flow of gases, the type of equipment used, and design considerations are very different for the two pressure regimes. It has further been shown that these different and often conflicting criteria are manifest in prior art apparatus.

Consequently, a single apparatus that can accurately measure the reaction, adsorption, and desorption of a gas with a solid at low, ambient, and high pressures is not present in the examples of prior art discussed above.

SUMMARY OF THE INVENTION

The object of the invention is to provide an apparatus and method for the very accurate measurement of the amount of gas adsorbed on or desorbed from a solid sample of surface area from about 0.01 to 1500 m²/g utilizing the volumetric method and to provide the apparatus with means for controlling and measuring the reaction, adsorption, and desorption of a gas with the sample over a wide range of flow, temperature, and pressure including pressures well below 1 atm and well above 1 atm. It is an object of this invention to provide an apparatus that can achieve pressures from $10^{-9}$ torr to 10,00 psia and flow rates from $8 \times 10^{-4}$ to $1.6 \times 10^3$ mL STP/s and temperatures from $-196°$ to $1650°$ C. It is a further object of this invention to achieve simultaneous control of pressure, flow, and temperature over these ranges. It is still a further object of this invention to provide means of unusually rapidly changing the pressure and temperature.

These and other objects of the invention are achieved in part by having an unusually small volume for that part of the apparatus for which the accuracy of adsorption or desorption measurements performed by the volumetric method increases with decreasing volume, the apparatus being highly leak tight, the apparatus being free of components in fluid communication with the reactor which significantly adsorb gas or outgas, the apparatus providing a robust glass reactor of extremely low leak and outgassing, the apparatus having both a high pressure transducer and a separate and very accurate low pressure transducer, the apparatus having novel configuration of valves and other components to enable very high and very low pressures to be rapidly and safely achieved, the apparatus providing means to very rapidly heat and cool a sample, providing means for the effluent from a reactor to be analyzed by a variety of devices which provide information on the composition of the effluent and hence also provide information on the reactions which occur in the reactor and the nature of the solid sample, and providing means for convenient access to the interior of the apparatus so as to increase it range of application.

The apparatus is useful for many types of characterization of solids which require measuring the amount of gas which is adsorbed on or desorbed from a solid. It is especially useful for accurate measurements of the equilibrium amount of gas adsorbed on or desorbed from a solid made the volumetric method. The apparatus is also useful for measuring the reaction of a gas, including gasified liquids and solids, with a solid, and especially a catalyst. The reactor can contain liquids or solids, and especially solid catalysts. Measurements can be made of many kinetic parameters of chemical reactions.

An object of this invention is to provide an improvement over prior art apparatus which perform these measurements. The improvement comprises the means to cover the low, ambient, and high pressure regimes in a single apparatus whereas prior art requires a plurality of apparatuses. An object of this invention is to provide means for these measurements to be made more quickly, at lower cost, and with less contamination than is achievable using multiple apparatuses. It is an object of this invention to provide an apparatus which in some instances enables measurements to made with much higher sensitivity and accuracy than by the aforementioned examples of prior art. It is an object of this invention to provide an apparatus with means to control temperature over a wider range than practiced by the aforementioned examples of prior art.

The nature of the invention can be most easily understood by reference to the example of research, development, and application of solid catalysts. Such materials are routinely characterized by apparatus which measure the adsorption and desorption of gases at pressures substantially less than 1 atm, but the reactivity of catalysts is routinely measured at pressures $\geq 1$ atm which requires a different apparatus. Each of these techniques can be performed on the preferred embodiment of this invention.

BRIEF DESCRIPTION OF THE DRAWINGS

FIG. 5 is a diagrammatic representation of an alternative embodiment of this invention;

FIG. 6 is a diagrammatic representation of an alternative embodiment of this invention;

The invention is not limited in its application to the details and construction and arrangement of parts illustrated in the company drawings since the invention is capable of other embodiments that are being practiced or carried out in various ways. Also, the phraseology and terminology employed herein are for the purpose of description and not of limitation.

AS SHOWN ON THE DRAWINGS

The present invention is inherently modular in nature and therefore there is a wide range of specifications which can be designed into it. Correspondingly, there is great lattitude in the choice of components to be used in the construction of the apparatus. Such flexibility in specification and design is in itself unexpected and is not possible with prior art machines. This flexibility is illustrated in the embodiments shown in FIGS. 1 to 7.

Figure 1:
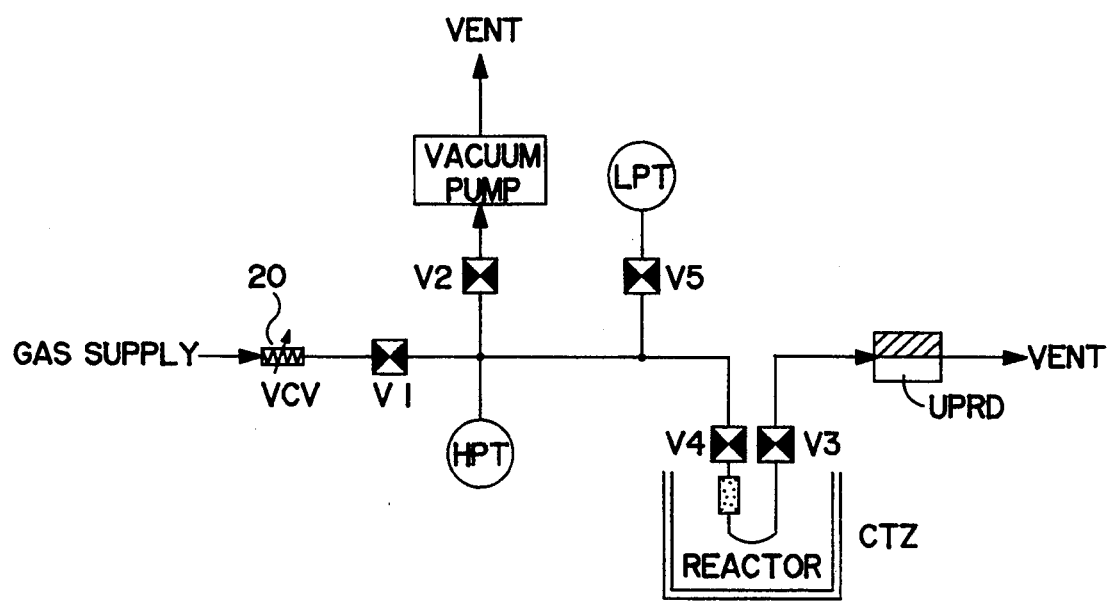
FIG. 1 is a diagrammatic representation of an alternative embodiment of this invention.
Figure 2:
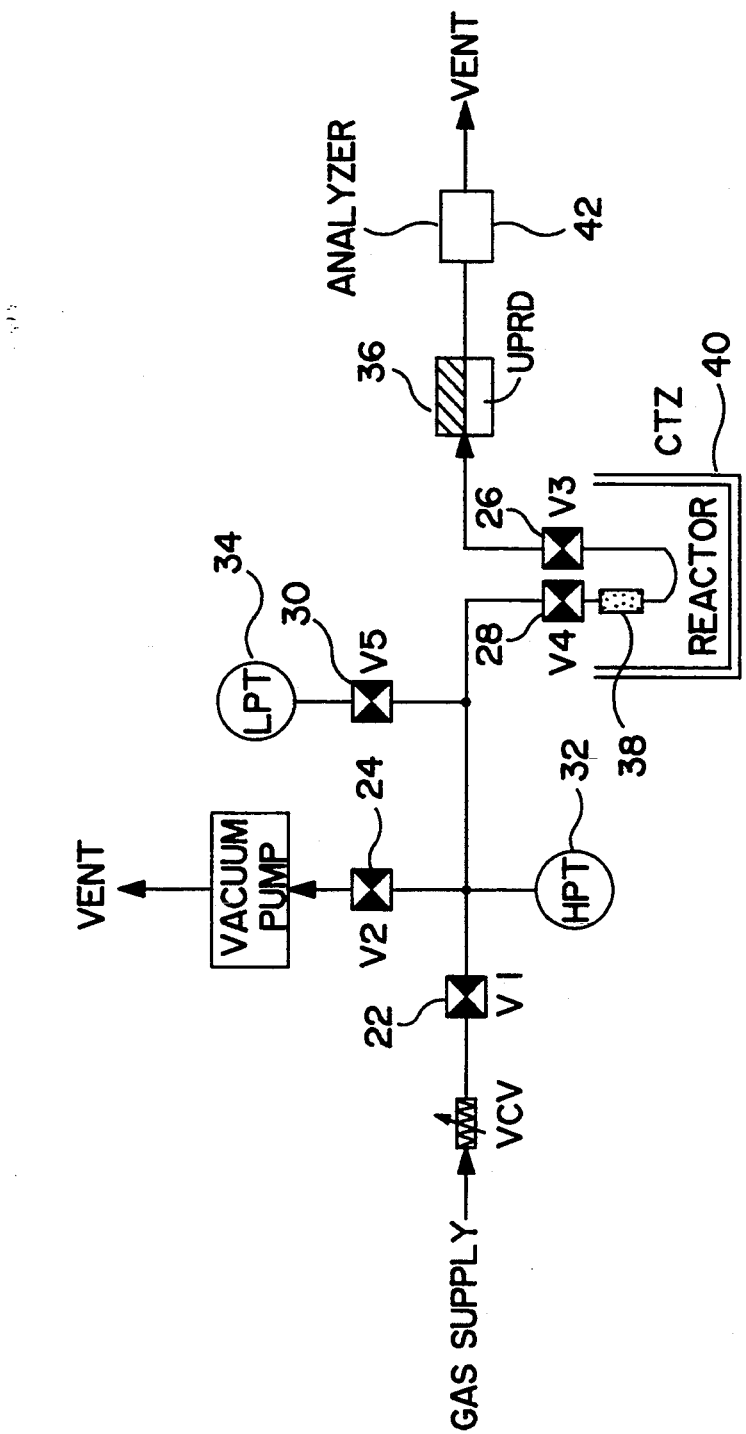
FIG. 2 is a diagrammatic representation of the preferred embodiment of this invention.
Figure 3:
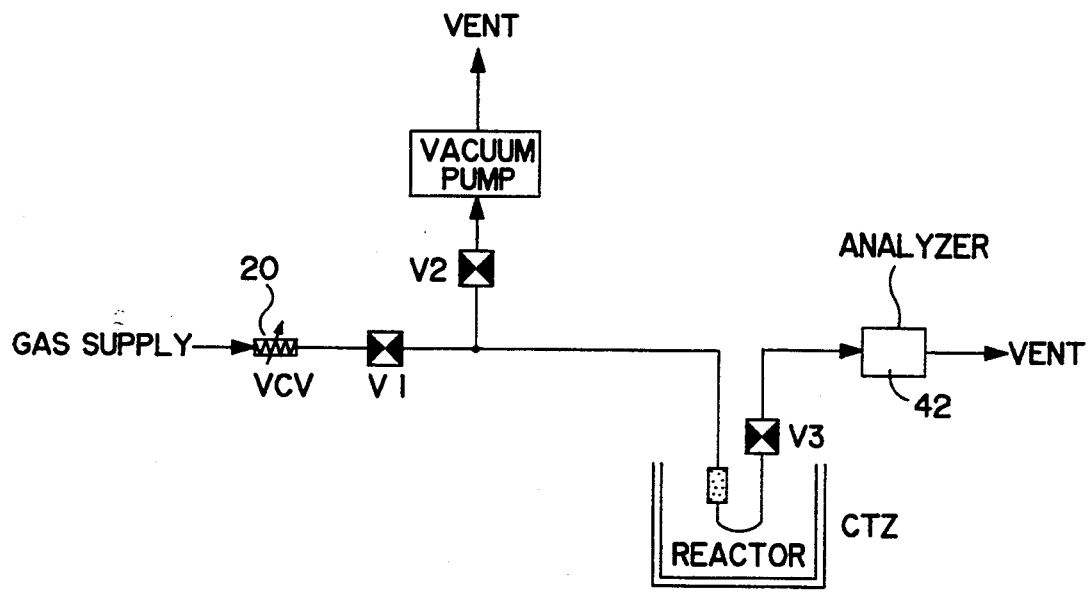
FIG. 3 is a diagrammatic representation of an alternative embodiment of this invention.
Figure 4:
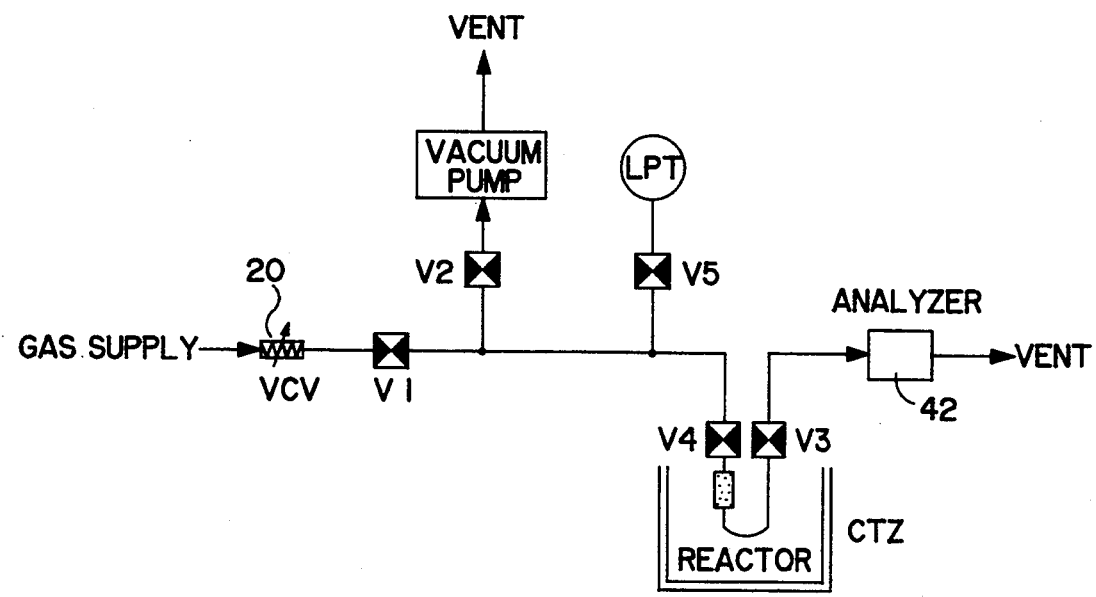
FIG. 4 is a diagrammatic representation of an alternative embodiment of this invention.
Figure 7:
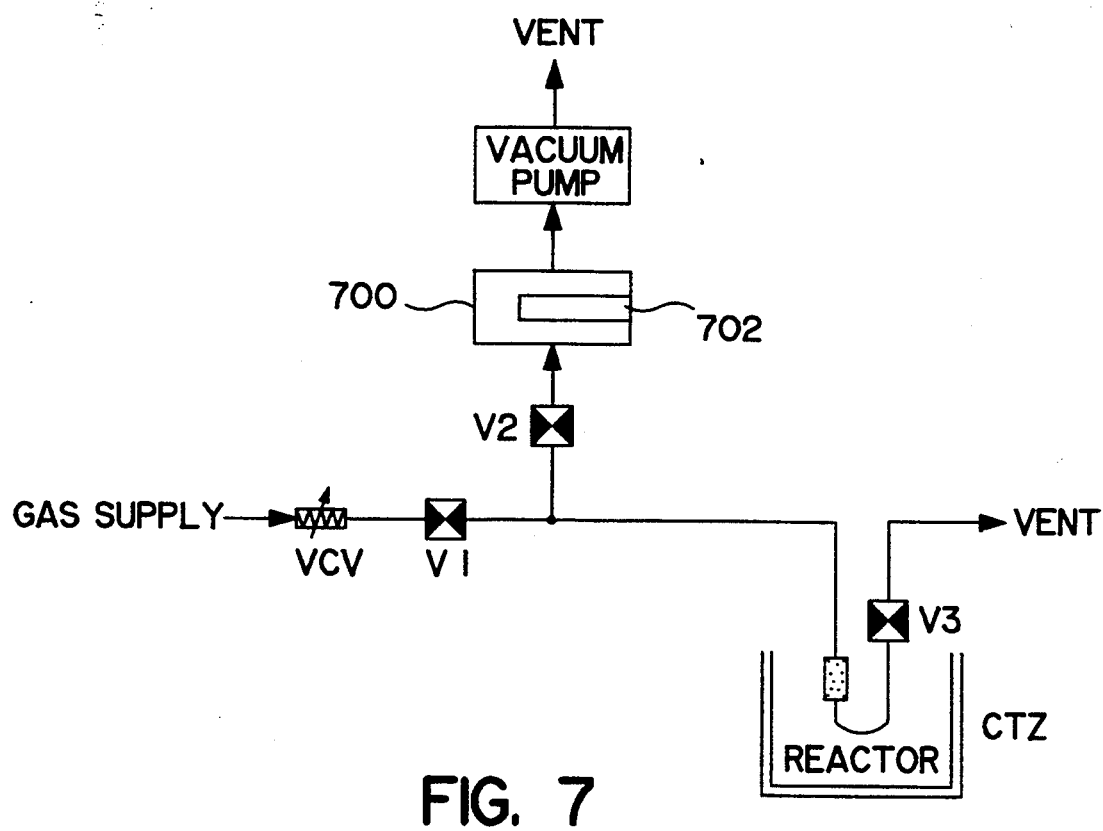
FIG. 7 is a diagrammatic representation of an alternative embodiment of this invention.
Figure 8:
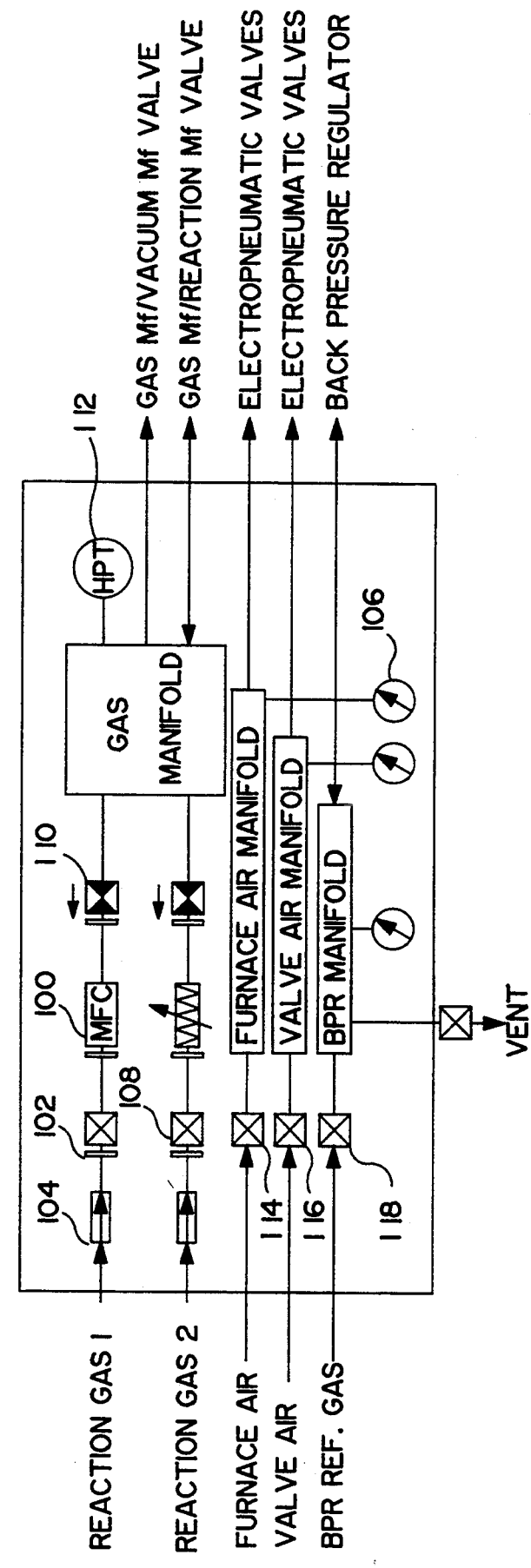
FIG. 8 is a diagrammatic representation of a portion of the preferred embodiment.
Figure 9:
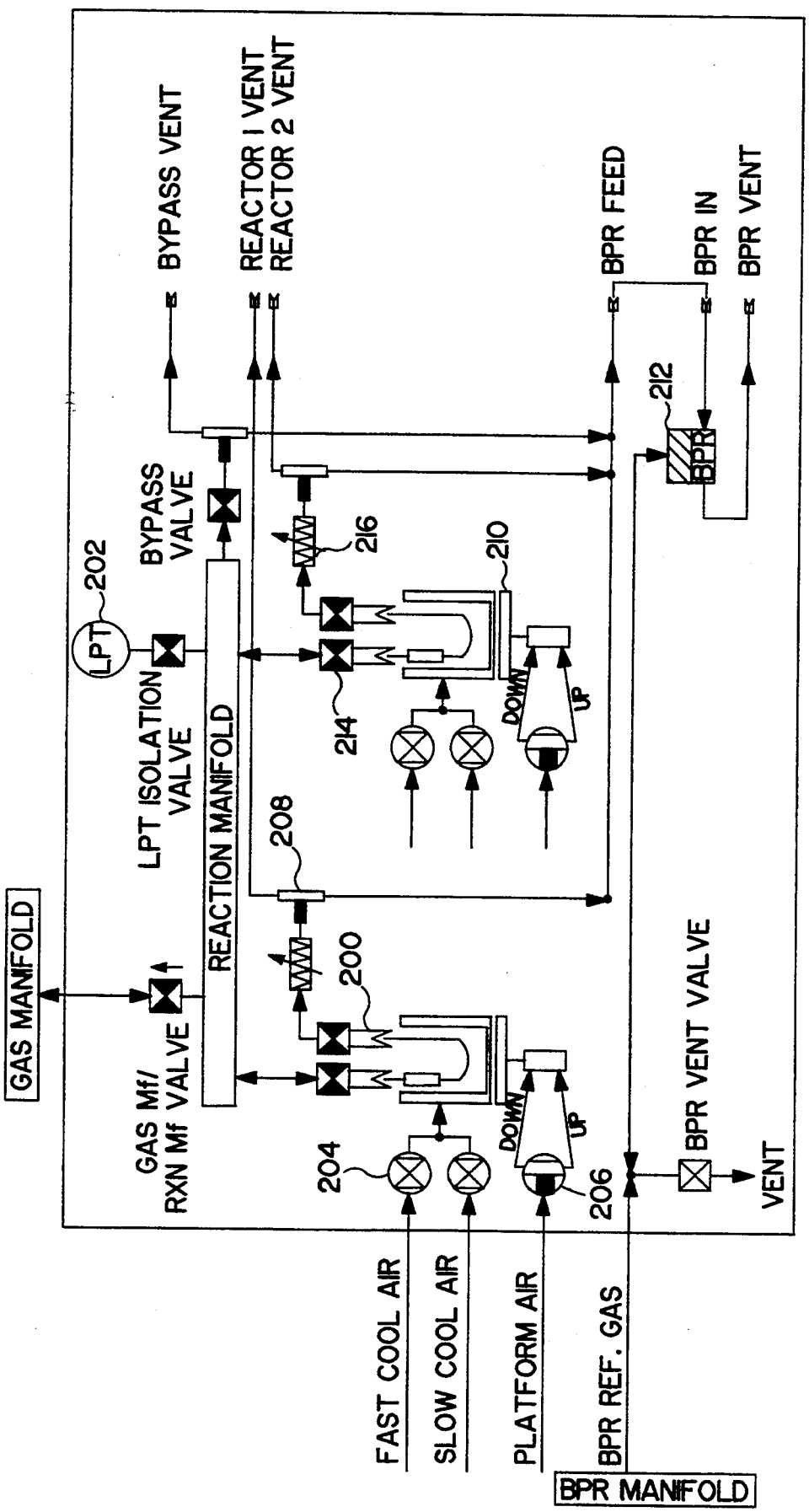
FIG. 9 is a diagrammatic representation of a portion of the preferred embodiment.
Figure 10:
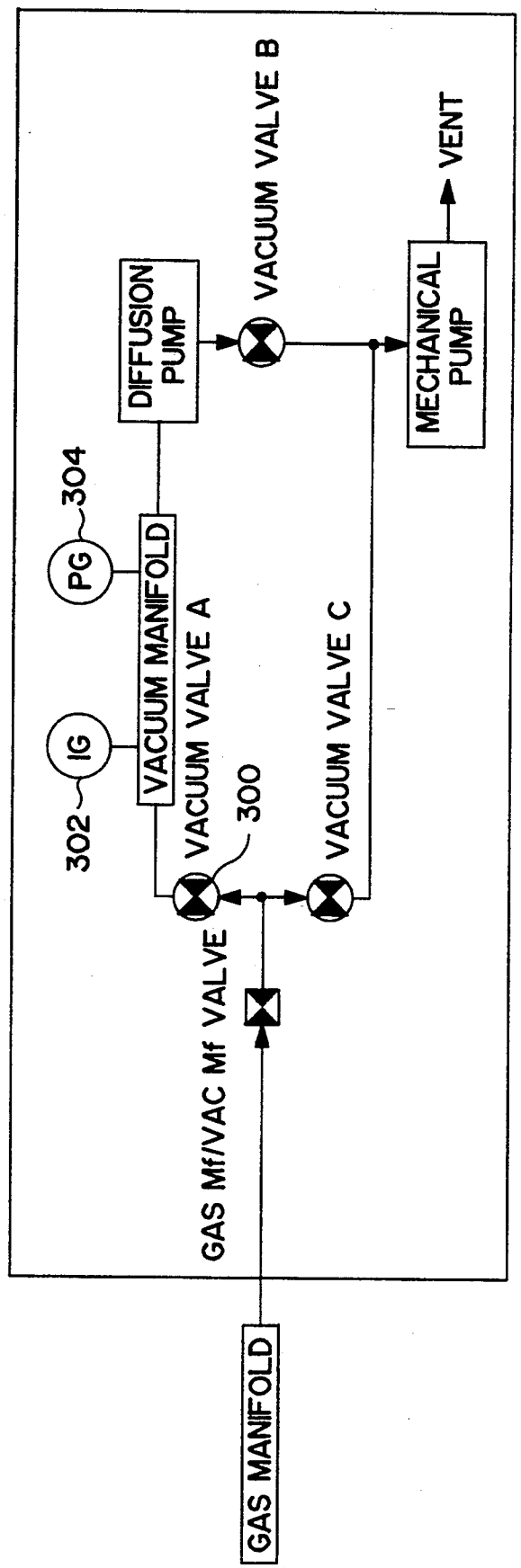
FIG. 10 is a diagrammatic representation of a portion of the preferred embodiment.
Figures 11, 12, 13:
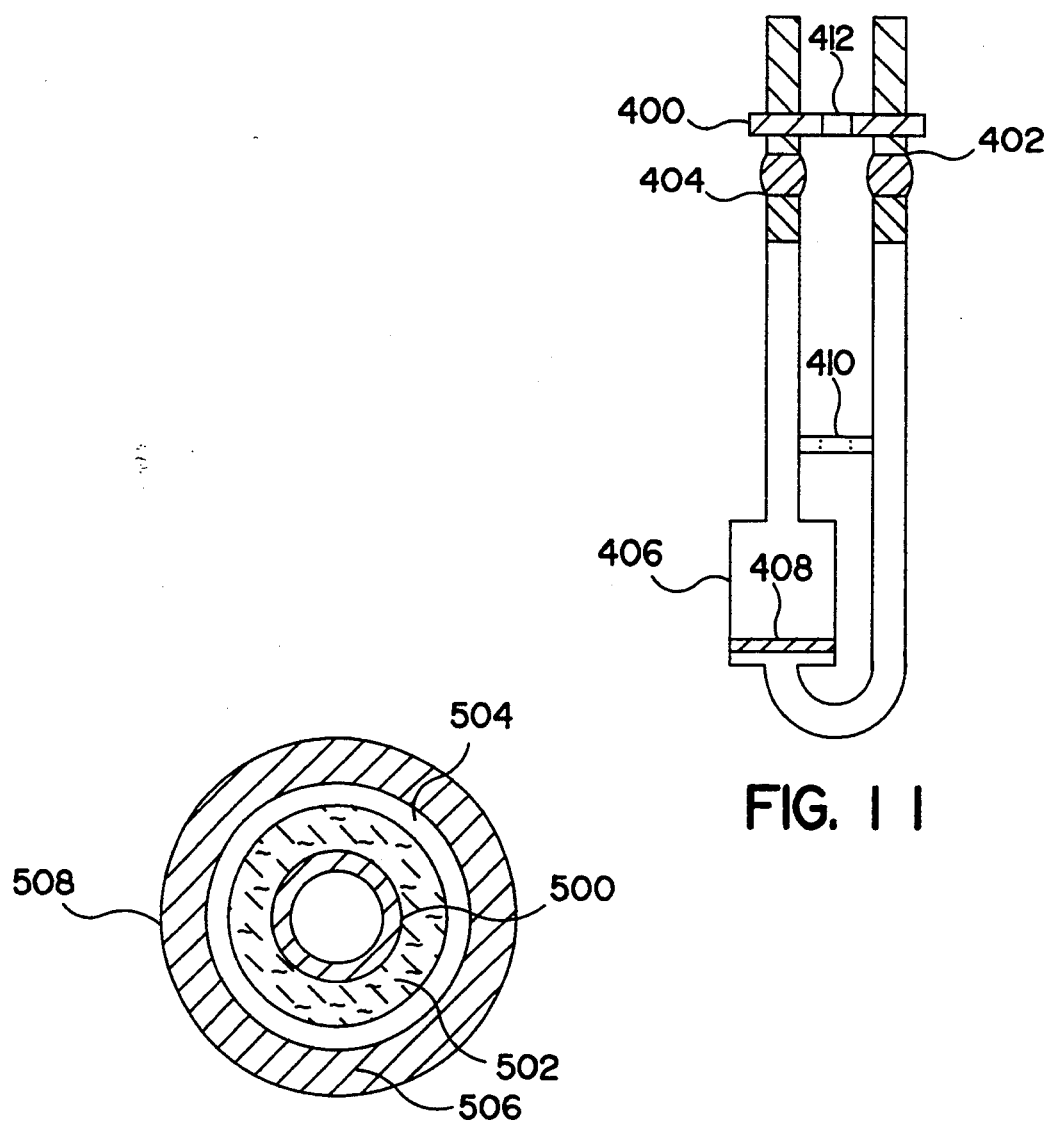
FIG. 11 is a diagrammatic representation of a glass reactor used in the preferred embodiment of this invention.
FIG. 12 is a diagrammatic representation of a furnace used in the preferred embodiment of this invention.
FIG. 13 is a diagrammatic representation of a reactor harness used in the preferred embodiment of this invention.

The following is a partial ist of the components shown on the diagrams and their abbreviated representations. In FIG. 1 there is a variable conductance valve, 20, designated on the drawing as VCV. In FIG. 2 there is a shutoff valve, 22, is designated V1. A shutoff valve, 24, is designated V2. A shutoff valve, 26, is designated V3. A shutoff valve, 28, is designated V4. A shutoff valve, 30, is designated V5. A high pressure transducer, 32, is designated HPT. A low pressure transducer, 34, is designated LPT. An upstream pressure regulating device, 36, is designated UPRD. An UPRD controls the pressure of gas upstream from it and allows the gas to flow through it, usually venting at atmospheric pressure. A reactor, 38, is designated Reactor. A reactor is a chamber to hold a solid sample. A controlled temperature zone, 40, is designated CTZ. A gas analyzer, 42, designated on the drawing as Analyzer. An Analyzer is a means of analyzing at least one parameter of a gas. In FIG. 3 there is a gas analyzer, 42, designated on the drawing as Analyzer. In FIG. 4 there is a gas analyzer, 42, designated on the drawing as Analyzer. In FIG. 5 there is a gas analyzer, 42, designated on the drawing as Analyzer. In FIG. 6 there is a gas analyzer, 42, designated on the drawing as Analyzer. In FIG. 7 there is an evacuable chamber, 700. A mass spectrometer probe, 702. In FIG. 8 there is a mass flow controller, 100, designated on the drawing as MFC. A mass flow controller electronically controls the mass flow rate of a gas. A filter, 102. A check valve, 104. A pressure gauge, 106. A shutoff valve, 108. A shutoff valve plumbed in a direction opposite to that normally done, 110. A high pressure transducer, 112. A shutoff valve, 114. A shutoff valve, 116. A shutoff valve, 118. In FIG. 9 there is a reactor harness, 200. A low pressure transducer, 202. A remotely actuated valve, 204. A remotely actuated selector valve, 206. A selector valve, 208. A pneumatic platform, 210. A back pressure regulator, 212, is designated BPR. A shutoff valve, 214. A metering valve, 216. In FIG. 10 there is a remotely actuated shutoff valve, 300. An ionization gauge, 302, designated on the drawing IG. A pirani gauge, 304 designated on the drawing PG. In FIG. 11 there is a bracket, 400. The bracket holds the metal tubes rigidly. A glass to metal seal, 402. A fused quartz to glass seal, 404. A sample chamber, 406. A frit of porous fused quartz, 408. A channel, 410. The channel aids in positioning a thermocouple inserted through the reactor bracket. A vertical channel and set screw, 412. This is used to position a thermocouple. In FIG. 12 there is a heating element, 500. Vacuum cast ceramic fiber insulation, 502. An annular cavity for the passage of cooling gas, 504. Outer insulation, 506. An outer shell, 508. In FIG. 13 there is an internal filter of large surface area, 600. A bracket for rigidly holding the two arms of the Reactor Harness, 602. A compression fitting to permit attachment of a reactor which is terminated with a tube, 604. A metal tube, 606.

The apparatus of FIG. 1 has means to accurately measure the amount of gas adsorbed on or desorbed from a solid utilizing the volumetric technique. This apparatus distinguishes from prior apparatus with this means in that this apparatus can also operate at high pressures and can perform and measure chemical reactions of a gas with a solid at low, ambient, and high pressures. This apparatus is a simplified embodiment of the apparatus of FIG. 2 and its operation and use are obvious from the description thereof.

The apparatus of FIG. 2 has means to accurately measure the amount of gas adsorbed on or desorbed from a solid utilizing the volumetric technique. This apparatus is similar to that of FIG. 1 except that a gas analyzer has been added. This apparatus distinguishes from prior apparatus with this means in that this apparatus can also operate at high pressures and can perform and measure chemical reactions of a gas with a solid at low, ambient, and high pressures, and has a gas analyzer suitable for analyzing the effluent from the reactor. This provides means to perform TPC of a solid sample at ambient and high pressures. The vacuum capability also provides means to evacuate gas lines to improve the performance of TPC and shorten the analysis time.

The method of using this apparatus to perform its various functions is obvious to those skilled in the art. Briefly, a solid sample is contained in the reactor. To measure the adsorption of a gas by the static pressure technique, the reactor is evacuated and valve 28 is closed. An adsorbate is then admitted to the primary dosing volume bounded by valves 22, 24, 28, and the low pressure transducer 34 and the high pressure transducer 32. Valve 28 is then opened to permit the gas to expand into the reactor. By comparing the drop in pressure to that which occurs for a nonadsorbing gas, usually He, the amount of gas which has adsorbed on the solid can be calculated. When equilibrium has been achieved, as evidenced by negligible further drop in the pressure, valve 28 is closed. The process can now be repeated to obtain multiple data points for the amount of adsorption versus pressure.

It has been noted that setting the pressure in the dosing volume is difficult using computer controlled valves if the pressure is below about 10 torr. In an alternative embodiment of the invention, a secondary dosing volume is added to the apparatus of FIG. 2. This consists of a volume which is much smaller than the primary dosing volume and which is isolatable from it. A preferred volume of the secondary dosing volume is about 2% to 10% of the volume of the primary dosing volume. To provide a dose of gas at an accurately known low pressure, gas is added to both of the dosing volumes. The secondary dosing volume is now isolated and the primary dosing volume evacuted. The gas in the secondary dosing volume is now expanded into the primary dosing volume, achieving a pressure of about 10 to 40-fold less than was originally in the primary dosing volume.

Still another alternative embodiment of the invention solves this problem by adding a secondary path to vacuum which is of low fluid conductance and in parallel with the path provided by valve 24. If the pressure in the dosing volume is too high, the pressure is reduced in a slow and controlled manner by evacuating with the secondary path. Evacuation with the primary path in a well designed apparatus can cause the pressure to drop from 760 torr to 1 torr in about 2 s, which is much to fast to control. At pressures below about 0.01 torr the speed of evacuation is slow enough that the pressure can be set using the primary path of evacuation. The conductance of the secondary path depends on the size of the primary dosing volume. It is adjusted to give a rate of evacuation of roughly 0.1 torr/s at a pressure of 1 torr. For finer control, a variable conductance leak valve can be used.

In a closely related method, an adsorbate isolated within the reactor is permitted to expand into the primary dosing volume. By comparing the drop in pressure to that which occurs for a nonadsorbing gas the amount of gas which has desorbed from the solid can be calculated.

TPC can be performed by flowing a gas over a solid sample and continuously monitoring the effluent with analyzer 42 as the temperature of the sample is raised at a controlled rate. By way of example, if temperature programmed reduction is being performed, then the gas could be 5% $H_2$ in Ar and the analyzer could be a thermal conductivity detector. If TPC is being performed at ambient pressure, then the best configuration is to have the analyzer 42 upstream of the upstream pressure regulating device 36. If TPC is being performed at high pressures, then the same configuration can be used up to the pressure limit of the detector. At higher pressures the configuration depicted in FIG. 2 is used. The upstream pressure regulating device 36 is readily set to control the pressure in the reactor at any value up to its rated pressure. To decrease contamination and shorten the equilibration time of the analyzer 42, prior to the start of TPC the gas lines between valves 22 and 26 can be evacuated.

Chemical reactions can be performed and measured in the flow mode in a manner similar to performing TPC. However, normally the temperature of the sample is kept constant and it is not necessary to continuously analyze the effluent. A very common arrangement is to use a gas sampling valve downstream of valve 26 to inject a pulse of the effluent into a gas chromatograph. In this case most of the effluent is vented, and only a small part is directed to the analyzer 42. If the reaction is at a pressure below the pressure limit of the gas sampling valve, then the gas sampling valve can be upstream of the upstream pressure regulating device 36. At higher pressures the configuration depicted in FIG. 2 is used. It is also sometimes desirable to place a gas sampling valve upstream of the reactor 38 so as to enable pulses of gas to be passed over a sample.

Reactions can also be done in the batch mode at pressures substantially below and substantially above 1 atm by using the low pressure transducer 34 or the high pressure transducer 32, respectively, to monitor the pressure of the reaction. For example, this is method is often used for monitoring the hydrogenation of a compound.

Methodology is also well developed for performing reactions in the flow mode at subambient pressures. Those skilled in the art could easily add an evacuation line from the exit of the upstream pressure regulating device 36 and use the output of the low pressure transducer 34 for the input of a control circuit to enable the upstream pressure regulating device 36 to control at subambient pressures. Similarly, the addition of a circulating pump and connections to the apparatus easily permits reactions to be performed in the circulating mode. However, reactions at low pressure and reactions in a circulating system are not of great importance in the field of catalysis.

The apparatus of FIG. 3 has means to perform TPC of a solid sample near ambient pressure. This apparatus distinguishes from prior apparatus with this means in that this apparatus also has means to evacuate gas lines to improve the performance of TPC and lower the analysis time, and means to perform and measure chemical reactions of a gas with a solid at low and ambient pressures. This apparatus is a simplified embodiment of the apparatus of FIG. 2 and its operation and use are obvious from the description thereof.

The apparatus of FIG. 4 has means to perform TPC of a solid sample near ambient pressure. This apparatus distinguishes from prior apparatus with this means in that this apparatus also has means to evacuate gas lines to improve the performance of TPC and lower the analysis time, means to perform and measure chemical reactions of a gas with a solid at low and ambient pressures, and means to accurately measure the amount of gas adsorbed on or desorbed from a solid utilizing the volumetric technique. This apparatus is a simplified embodiment of the apparatus of FIG. 2 and its operation and use are obvious from the description thereof.

The apparatus of FIG. 5 has means to perform TPC of a solid sample near ambient pressure. This apparatus distinguishes from prior apparatus with this means in that this apparatus also has means to evacuate gas lines to improve the performance of TPC and lower the analysis time, means to perform and measure chemical reactions of a gas with a solid at low, ambient, and high pressures. This apparatus is a simplified embodiment of the apparatus of FIG. 2 and its operation and use are obvious from the description thereof.

The apparatus of FIG. 6 has means to perform TPC of a solid sample near ambient pressure. This apparatus distinguishes from prior apparatus with this means in that this apparatus also has means to perform TPC at high pressures, and has means to perform and measure chemical reactions of a gas with a solid at ambient and high pressures. This apparatus is a simplified embodiment of the apparatus of FIG. 2 and its operation and use are obvious from the description thereof.

The apparatus of FIG. 7 has means to perform temperature programmed desorption by the direct evacuation method on solid samples of very small surface area. This apparatus distinguishes from prior apparatus with this means in that this apparatus also has means to use samples of very large surface area, the sample is contained in a conventional reactor in contact with air rather than the reactor being inside the evacuated chamber containing the mass spectrometer probe, and this apparatus has means to perform chemical reactions of a gas with a solid at low and ambient pressures.

The method of using this apparatus to perform temperature programmed desorption by the direct evacuation method would be obvious to those skilled in the art. Briefly, a solid sample is contained in the reactor. The sample is exposed to an adsorbate. The vacuum pump is then used to evacuate the reactor and simultaneously the temperature of the sample is raised at a controlled rate and desorbed gas is continuously analyzed by the mass spectrometer probe.

FIG. 8 depicts the gas inlet system used in the preferred embodiment of this invention. Detailed description is contained in a following section. By way of example, inlets for two reaction gases are depicted.

FIG. 9 depicts the reaction system used in the preferred embodiment of this invention. Detailed description is contained in a following section. In order to illustrate certain fluid paths which are unique to an embodiment of the invention which can simultaneously utilize more than one reactor, FIG. 9 depicts an apparatus which can simultaneously use two reactors. The invention can simultaneously use substantially more reactors with only slight degradation of its speed of evacuation and accuracy for measuring the amount of gas adsorbed on or desorbed from a solid sample utilizing the volumetric method. Other specifications of the invention described herein are not affected by additional reactors.

FIG. 10 depicts the vacuum system used in the preferred embodiment of this invention. Detailed description is contained in a following section.

FIG. 11 depicts the glass reactor used in the preferred embodiment of this invention for measuring the amount of gas chemically adsorbed on or desorbed from a solid sample and for performing chemical reactions in the flow-through mode at pressures near ambient. This reactor distinguishes from prior art glass reactors used with apparatus for measuring the amount of gas adsorbed on or desorbed from a solid in that it is highly resistant to breakage, can be attached to a metal coupling without the use of any elastomers, and has a high fluid conductance for evacuation. The metal ends prevent breakage of the open ends of a glass reactor when it is attached to compression fittings on the Reaction Harness and also allow the use of metal fittings which are much more leak tight and free of degassing than the elastomeric connections which are otherwise required when connecting a glass tube. This increases the accuracy of the apparatus for measuring the adsorption and desorption of gases by the volumetric technique.

The metal ends are held rigid by a reactor bracket which serves to both accurately position the ends of the reactor and to prevent torque, generated when attaching a reactor to the Reactor Harness, from being transmitted to the glass and causing it to break. A preferred reactor bracket is made of SS and is soldered to the metal terminations so as to hold them rigid. Still another alternative embodiment adds a vertical hole 412 in the bracket and a horizontal set screw so as to position a thermocouple which extends vertically through the bracket so as to provide means to position the sensing end of the thermocouple next to the sample chamber.

Another alternative embodiment of this reactor adds a channel 410 to help position a thermocouple, said channel being formed by two pieces of fused quartz bridging across the arms of the reactor. Still another alternative embodiment has each open end of the reactor terminated with a fitting suitable for coupling to other fittings. Examples are SWAGELOK, VCR, and VCO fittings.

The preferred size of this reactor is a sample chamber of about 3 to 50 mm I.D., metal tubulation of about 1/16" to 1" O.D., quartz and glass tubing above the sample chamber of about 2 to 50 mm I.D., and quartz and glass tubing below the sample chamber and extending up the opposite arm of the reactor of size about 1 to 20 mm I.D. A more preferred size is a sample chamber of about 3 to 25 mm I.D., metal tubulation of about ⅛" to ½" O.D., quartz and glass tubing above the sample chamber of about 3 to 13 mm I.D., and quartz and glass tubing below the sample chamber and extending up the opposite arm of the reactor of size about 1 to 10 mm I.D.

When the sample being analyzed has a large diameter, it is necessary for the tubing going to the sample chamber to have a large I.D. This can seriously degrade the accuracy of measurements of the amount of gas adsorbed on or desorbed from a solid utilizing the volumetric method. An improvement is to add a glass insert which fills the space above the sample. A preferred insert is made of fused quartz tubing of with the ends sealed shut. The insert should be of such diameter that there is about a 0.3 to 1 mm annular space between it and the inner wall of the reactor. For a typical size reactor holding a pellets of a spherical sample of 1 cm O.D., the glass insert will reduce the dead volume of the reactor by about 10 mL and therefore increase the accuracy of the measurements by about 30%.

FIG. 12 is a cross sectional depiction of the furnace used in the preferred embodiment of this invention. For simplicity, ports for the entry and exit of gas are not shown. Also, the furnace depicted is of the tube type, but other types, including a split tube furnace, are readily constructed. The furnace distinguishes from prior art furnaces used with apparatus for measuring the amount of gas adsorbed on or desorbed from a solid in that it can be heated and cooled very rapidly and can operate at higher and lower temperatures. It is also very light weight and the surface remains cool even when heated to extremely high temperatures, which facilites rapidly removing the furnace. Heating elements are near the inner surface of insulation which is lightweight and of low K. factor, which also gives very fast thermal response. A preferred heating element consists of a KANTHAL wire embedded in vacuum cast alumina fiber insulation, providing an upper temperature limit of 1200° C. An alternative embodiment uses a SiC heating element which increases the temperature limit to 1650° C. Between the heating elements and the outer insulation is at least one annular space to which a controlled flow of a gas, typically air or a cryogenic gas, can be directed. The gas enters through a metal tube at the top of the furnace and exits through holes in the bottom. Alternative porting arrangements can also be successfully used.

As will be shown in the Examples, both the use of cooling air in an annular space and an ultra light weight insulation to support the heating element is required to achieve exceptional thermal response. The use of only the special insulation gives faster heating than for a conventional ceramic support, but the outer surface of the furnace will become quite hot if the furnace is at temperatures substantially above 500° C. Therefore, in order to avoid using a furnace of large diameter and correspondingly slower response, it is necessary to pass cooling air through the annular space while the furnace is heating. This is sharply distinguished from the common practice of passing air through a furnace in order to cool it after a heating cycle. Further, the use of an inner core of insulation is necessary to shield the hot inner core of the furnace and to avoid preferential cooling of the low thermal mass thermocouple in the furnace. The improvement is amplified by also using a fan to blow air against the outer surface of the furnace. Maximum performance can be achieved by using two annular channels, but this is not normally needed. The inner space is adjacent to the outer surface of the insulation supporting the heating element. Gas flow in this space serves to quickly cool the heating element. The outer space is adjacent to the shell of the furnace. Gas flow in this space maximizes the cooling of the shell. In another alternative embodiment the outer insulation 506 is omitted.

A preferred size for the radial width of the annular space is ⅛ to 2", and a more preferred size is ¼ to ½'. The size of a preferred furnace depends on the size of reactor it is to heat. A preferred furnace size suitable for the typical amount of sample (usually 0.1 to 5 g) used for adsorption and desorption measurements is about 4 to 6" O.D. and 7 to 12" long. The use of a cryogenic gas in the air lines allows time programmable temperatures down to −100° C. to be achieved. A preferred source of cryogenic gas is from a tank of liquid $N_2$. An alternative source is compressed $CO_2$.

FIG. 13 depicts the Reactor Harness used to attach a reactor to the preferred embodiment of this invention. FIG. 13 is a cutaway view which depicts the internal high surface area filters. The reactor harness enables a means of attaching a reactor to an apparatus for measuring the amount of gas adsorbed on or desorbed from a solid. The Reactor Harness avoids wear on the fittings of shutoff valves 26 and 28 of FIG. 2 which would otherwise be normally used to attach a reactor and it also traps particulate matter without significantly slowing the evacuation of the reactor or adding dead volume to the apparatus. Slight distortion of the fittings can seriously degrade the vacuum capability of an apparatus, and replacing a valve is much more difficult than replacing the reactor harness. The reactor harness also contains unusual filters to protect the apparatus against particulate matter without significantly increasing the time necessary to evacuate a reactor. The preferred Reactor Harness consists of two pieces of SS tubing with appropriate end connections. Each side of a Reactor Harness also has a special porous SS filter of large surface area and no dead volume to minimize the chance of particulate matter entering the Reaction Manifold. A preferred Reactor Harness consists of type 316 SS tubing which is between $\frac{1}{8}''$ and $\frac{1}{2}''$ O.D. and has an internal, cylindrical type 316 SS porous filter with a surface area of at least 0.2 sq. in. and a porosity of 1 to 100 microns. A more preferred reactor harness consists of $\frac{1}{4}''$ to $\frac{1}{2}''$ O.D. tubing with an internal filter of surface area 0.3 to 2 sq. in. and a porosity of 5 to 20 microns. An example of such a filter is type 6610 manufactured by Mott Metallurgical Corp. of Farmington, Conn.

An alternative embodiment adds a port on each arm of the Reactor Harness. A port is normally sealed with a cap, but can be used to provide an additional path for the introduction or removal of solids, liquids or gases from a reactor. The addtion of two ports on one side of the Reactor Harness and a blockage between them enables gas flowing from the Reaction Manifold to exit the apparatus, interact with a variety of external devices including a means of introducing a liquid feed, a gas sampling valve, or a mixing volume, and then reenter the apparatus. A Reactor Harness can also accommodate a wide range of fittings on each end. The tube terminations on one end and the SWAGELOK fittings on the other end depicted in FIG. 13 are suitable for many valves which are terminated with female SWAGELOK fittings.

The preferred embodiment of this invention consists of components combined in a novel manner as to achieve the following capabilities. (1) Pressure range of about from $10^{-9}$ torr to 1500 psia. (2) The ability to direct the flow of one or more gases into or through one or more reactors. (3) Time programmable temperature control over the range from about $-100°$ C. to $1200°$ C. (4) Automatic control of the flow rate of reaction gases. (5) Temperature control down to $-196°$ C. (6) Unusually rapid heating and cooling of a furnace. (7) Ability to automatically raise and lower a furnace or an insulated container about a reactor. (8) Ability to very rapidly switch between the use of a furnace and insulated flask, thereby achieving unusually rapid cooling of a reactor since it is not necessary to also cool the furnace. (9) Accurate measurement of the pressure in the each of the ranges of about 0 to 1000 torr and 0 to 1,500 psia, achieved by utilizing two accurate pressure transducers, one for each pressure range. (10) Unusually high accuracy for measuring the amount of gas adsorbed on or desorbed from a solid when done utilizing the volumetric technique, achieved by using various improved components and novel configuration of components. (11) Unusually fast evacuation of the reactor. (12) Remote actuation of the vacuum valves. (13) Ability to use solid samples of surface area from about 0.01 to 1500 $m^2/g$, powders, porous solids, and sample sizes of about 1 mg to 200 g. (14) Protection of the valves from particulate matter achieved without significant affect on the pumping speed of the apparatus. (15) The ability to individually control and measure the flow of a reaction gas in each of a plurality of reactors through which it is simultaneously passing. (16) The unusual ability to rapidly switch the pressure of a reaction gas from 1 atm to high pressure. (17) The ability to attach a glass reactor to the apparatus without breakage or the introduction of elastomeric materials. (18) The unusual ability to easily test the system for leaks and enable the safe use of shutoff valves which are plumbed in a backwards manner, achieved by the use of a redundant set of shutoff valves where the gas enters the apparatus. (19) The capability to analyze the reactor effluent. (20) Easy modification and maintenance of the apparatus, provided by the use of a novel enclosure.

A detailed description of the preferred embodiment of the present invention follows. The complex arrangement of components can be simplified by considering the machine to be composed of systems and manifolds. A system is defined as a major group of components that act together as a unit. A manifold is defined as an elongated conduit for the transport of gas which interconnects a number of components. For each of the FIGS. 8 through 10, lines and arrows show the normal direction of gas flow. A small arrow next to a valve indicates that the valve is plumbed in a direction opposite to that normally done. Parts outside of the rectangle are included to help show the interrelationship of the systems.

The preferred embodiment consists of five systems: Gas Inlet System, Reaction System, Vacuum System, Analyzer System, and the Computer System. Each manifold is contained within a system and is described therein.

The Gas Inlet System, FIG. 8 accepts gas from a supply and directs it to the appropriate manifold. The Gas Inlet System also controls the flow rate of gases which enter the Gas Manifold. Metal tubing used in the preferred embodiment is stainless steel (SS). Tubing and fittings with a pressure rating of 10,000 psia are readily available, for example from the Swagelok Co. of Solon, Ohio. In an alternative embodiment, any of a large number of other metals can be used which are well known to those skilled in the art. This includes less common materials such as TEFLON lined SS and glass lined SS.

A check valve 104 is attached to the inlet side of the shutoff valve for each reaction gas. A preferred check valve is constructed of type 316 stainless steel, has a VITON seat, and has a pressure rating of at least 1500 psia.

A packed shutoff valve 102 is directly attached to each reaction gas supply. Three additional valves control the gas supplies for the Furnace Air, Valve Air, and Back Pressure Regulator (BPR) Manifolds. The valves for the reaction gases are redundant, since another valve is supplied for each gas which enters the Gas Manifold. These extra valves are provided for safety and as an aid in leak testing. These valves enable bellows valves to be safely plumbed in a novel and backwards direction, which substantially improves the performance of the machine with respect to the speed of evacuation and the accuracy of measuring the adsorption and desorption of gases. A preferred shutoff valve is constructed of type 316 SS with a Teflon packing and has a pressure rating of at least 1500 psia.

The rate of flow of a reaction gas entering the Gas Manifold is preferably controlled by a mass flow controller 100 (MFC). A preferred MFC is constructed of type 316 SS with VITON O-rings, has a pressure rating of 1500 psia, is tested to have a leak of $<4\times10^{-9}$ mL (STP)/s, and has a flow capacity suitable for the processes to be monitored. MFC are commercially available which can control flow from $8\times10^{-4}$ to $1.6\times10^3$ mL (STP)/s. In some applications equally good performance can be achieved using a metering valve. A preferred metering valve is constructed of type 316 SS with a VITON packing, has a pressure rating of 1500 psia, and has a flow capacity suitable for the processes to be monitored. At this time the highest pressure rating of an MFC is 3500 psi. An example is model 5850E manufactured by Brooks Instrument of Hatfield, Pa.

A bellows shutoff valve 110 controls the entry of each reaction gas into the Gas Manifold. Bellow valves have extremely low leak levels. A bellows shutoff valve has a direction of gas flow stamped on the body by the manufacturer. This directionality arises as a safety feature, since the bellows is the weakest part of the valve and is exposed to the upstream gas supply even when the valve is closed. However, examination of the insides of such a valve reveals that almost all of the internal volume is contained on the side of the valve seat having the bellows. The total internal volume of a preferred bellows valve is about 1 to 4 mL. Therefore, plumbing a bellows valve backwards results in a substantial reduction in the volume of the manifold to which it is connected. Lowering the internal volume of a manifold proportionately increases the accuracy of adsorption and desorption measurements and reduces the time to evacuate the manifold. A preferred embodiment of the invention has each of the bellows type valves for reaction gases which are attached to the Gas Manifold plumbed in a backwards direction. This novel configuration can be safely done due to the presence of redundant shutoff valves upstream of the bellows valves. The preferred bellows valve is constructed of type 316 SS, has a stem tip of SS, and has a pressure rating of at least 1500 psia. An example of such a valve is model 4A-P4R-SS manufactured by the Parker Corp. of Huntsville, Ala. Still another alternative embodiment are similar valves which are remotely actuated. Such valves provide means of computer controlled operation. An example is the HB series valves manufactured by the Nupro Co. of Willoughby, Ohio.

The Gas Manifold is a piece of narrow bore stainless steel tubing to which various components are attached. A preferred Gas Manifold is constructed of type 316 SS tubing of $\frac{1}{8}$ to 1" O.D. and has a pressure rating of at least 1,500 psia. A more preferred Gas Manifold is constructed of tubing in the range of 0.25" O.D.$\times$0.15" I.D. to 0.5" O.D.$\times$0.3" I.D.

An accurate high pressure transducer 112 is attached to the Gas Manifold and continuously monitors the pressure in the Gas Manifold. A preferred HPT is a capacitance type gauge constructed of SS of low internal volume ($<10$ mL) with a range of 0 to 1500 psia and an accuracy of 0.1% of full scale. An example is model 204 manufactured by Setra Systems Inc. of Acton, Mass. Safety considerations suggest an alarm if the pressure in the Gas Manifold exceeds its rated value. A preferred embodiment of the invention uses the output of the HPT as part of a circuit which will activate an alarm if the pressure exceeds 1,500 psia. In an alternative embodiment of this invention, this high pressure transducer or a second one is placed downstream of the reactor. High pressure transducers with a range up to 10,000 psia are available from Setra Systems.

Air which passes through the Furnace Air Valve 114 enters the Furnace Air Manifold. As a safety feature, a pressure gauge 106 continuously displays the pressure in the Furnace Air Manifold. A preferred Furnace Air Manifold is constructed of brass of approximately 0.5" O.D.$\times$0.2" I.D. and has a pressure rating of at least 100 psia.

Air which passes through the Valve Air Valve 116 enters the Valve Air Manifold which then directs the air to a control vive to actuate a vauum valve. As a safety feature, a pressure gauge continuously displays the pressure in the Valve Air Manifold. A preferred Valve Air Manifold is constructed of brass of approximately 0.5" O.D.$\times$0.2" I.D. and has a pressure rating of at least 150 psia.

Opening the BPR Pressurize Valve 118 admits the gas used to set the reference pressure of the BPR to the BPR Manifold and to the regulating dome of the BPR. A tube also goes to the BPR Reference Pressure Gauge which continuously displays the pressure in the BPR Manifold. A preferred BPR Manifold is constructed of copper, brass, or SS of 1/16" to $\frac{1}{4}$" O.D. and has a pressure rating of at least 1,500 psia.

Numerous conventional porous metal disc type filters 102 are present in the Gas Inlet System. A preferred filter is constructed of type 316 SS and is of 0.5 to 50 microns porosity. The most preferred filter is of porosity 1 to 20 microns.

The Reaction System, FIG. 9 accepts gas from the Gas Manifold and directs it to the appropriate reactor and vent. The Reaction System also controls the pressure of reaction gases within the machine, controls the temperature of reactors, and provides very accurate measurement of the pressure in the Reaction Manifold in the range of 0 to about 1000 torr.

The Reaction Manifold is a piece of narrow bore stainless steel tubing to which various components are attached. A small I.D. of the Reaction Manifold is preferred in order to lower its internal volume and thus increase the accuracy of adsorption and desorption measurements. However, a small I.D. slows evacuation. A clever choice so as to minimize the internal volume without significantly increasing the evacuation time is to have I.D. of the Reaction Manifold about 60% of the I.D. of the Gas Manifold. A preferred Reaction Manifold is constructed of type 316 SS tubing of size $\frac{1}{8}$ to 1" O.D. and has a pressure rating of 1,500 psia. A more preferred Reaction Manifold is constructed of tubing of size 0.25" O.D.$\times$0.06" I.D. to 0.5" O.D.$\times$0.3" I.D.

A very accurate low pressure transducer 202 (LPT) is provided to measure the pressure in the Reaction Manifold in the range of about 0 to 1000 torr. A preferred LPT has a low internal volume ($<10$ mL), is constructed of SS and an accuracy of at least 0.1% of FS. A more preferred LPT has an accuracy of from 0.02% to 0.15% of reading. An example is the model 390 manufactured by MKS of Andover, Mass. An alternative embodiment is to use two or more LPT's so as to achieve higher accuracy in the low pressure range. Extremely accurate LPT's are available with full scale ranges of 1, 10, 100, and 1000 torr are manufacured by MKS.

The low pressure transducer will be damaged if the pressure to which it is exposed exceeds about 1250 torr. For this reason it is protected by the LPT Isolation Valve. Safety considerations suggest an alarm if the pressure in the Reaction Manifold exceeds the rated value of the LPT. This warns the operator to close the LPT Isolation Valve. The preferred embodiment of the invention uses the output of the HPT as the input of an electronic circuit which will activate an alarm if the pressure exceeds 1,000 torr. Such circuits are well known to those skilled in the art of electronics. The preferred and alternative LPT isolation valves are a bellows type valve as described previously.

A variety of valves direct the flow of the reaction gases. Of particular importance, the Gas Manifold/Reaction Manifold Valve is a supplemental shutoff valve which separates the two manifolds. This novel implementation lowers the volume of gas whose pressure is being measured by the LPT by about 2-fold, and consequently increases the accuracy of adsorption and desorption measurements made by the volumetric technique by about 2-fold. It also enables an unlimited number of gas ports on the Gas Manifold without affecting the accuracy of such adsorption measurements. This valve is also plumbed in a backwards direction, which further reduces the volume of gas in the Reaction Manifold and provides advantages previously described.

A Bypass Valve provides a fluid path to vent without passing through one of the reactors. The Bypass valve is used to establish baseline conditions of flow and analyzer before starting a flow of gas through a reactor. Gas flowing through the Bypass valve can be directed either to the BPR or to Vent.

Each shutoff valve 214 attached to a reactor harness provides means for gas to flow from the Reaction Manifold into a reactor, into and through a reactor, and isolates a reactor from fluid communication with the Reaction Manifold and the reactor vent. A metering valve 216 on the exit of each reactor provide means for gas which is simultaneously flowing through more than one reactor to be partitioned in any ratio between the reactors. A 3-way valve 208 provide an unusually rapid means of controlling whether the effluent will be to a vent or through the BPR. The preferred valve and alternative embodiments for the Gas Manifold/Reaction Manifold Valve, Bypass Valve, and the two valves proximate to a reactor are bellows type valves as described previously. The preferred metering valve and alternative embodiments are as previously described. The preferred 3-way valve is constructed of type 316 SS with a Teflon packing and has a pressure rating of 1500 psia. It is to be noted that in the preferred embodiment of this invention all valves which are in fluid communication with a sample during a measurement of adsorption or desorption of gas by the volumetric method are packless.

A Reactor Harness 200 is attached to the pair of inlet and outlet valves which are proximate to a reactor. The preferred Reactor Harness is depicted in FIG. 13.

A large variety of glass and metal reactors can be attached and removed from the apparatus. The preferred choice of reactor depends on the type of measurement being made. Chemisorption measurements, TPC, and many reactions are normally done in a flow-through reactor. The preferred glass reactor for chemisorption measurements is shown diagramatically in FIG. 11. If measurements of the adsorption or desorption of gas with a solid are being performed, then a preferred volume is 0.5 to 50 mL, and a more preferred volume is 1 to 20 mL.

A bulb type reactor having a common port for the entry and exit of gas is commonly used for physisorption measurements. These are well known to those familiar with the art of physisorption measurements.

A preferred metal reactor is constructed of type 316 SS tubing and has a pressure limit of 1,500 psia. Most commonly this is a conventional tube reactor with narrow bore tubing welded to the bottom and bent into a U shape so both the inlet and outlet ports can be easily connected to the Reaction Harness. A pressure rating of 10,000 psia is readily achieved.

An improvement of this invention is that almost any laboratory scale reactor can be attached to the Reactor Harness by using metal tubing and fittings. Examples of such alternative embodiments are a tubular reactor, stirred autoclave, continuous stirred tank reactor, BERTY reactor, fluidized bed reactor, and slurry reactor. Such reactors are manufactured by a variety of companies including Parr Instruments of Moline, Ill. and Autoclave Engineers of Erie, Penn.

The furnace used with the preferred embodiment of this invention is depicted in FIG. 12. The furnace is of novel design, having means for extremely fast heat up and cool down. A fan blows a high volume of air across the outer surface of a furnace, thereby greatly lowering the surface temperature from what it would otherwise be. At high temperatures, a flow of air is also passed through an annular space to further lower the shell temperature. The fan and internal air flow therefore allow a furnace to be constructed with much less insulation and hence much smaller thermal mass than would otherwise be possible. A preferred embodiment of the invention uses a fan with an air flow of about 20 to 250 cfm, and a more preferred embodiment uses a fan with an air flow of about 70 to 150 cfm.

The preferred embodiment of the invention utilizes a novel combination of two different gas flows to the annular space of a furnace, each controlled by a remotely actuated valve. One flow is smaller, termed Slow Air, and the other is larger, termed Fast Air. A flow of Slow Air can be continuously maintained during a heating cycle and serves to further lower the outer skin temperature of a furnace, providing the advantage previously described. The Fast Air flow can further enhance this effect and is especially used to greatly increase the rate of cooling of the furnace. In the preferred embodiment of this invention the gas flows are remotely controlled by the second output of a dual output temperature controller. This output can have proportional control, thereby minimizing temperature overshoot which allows unusually high rates of heating to be controlled and permits temperature programmed cooling. A preferred ratio of the rate of Fast Air flow to Slow Air flow is 1:1 to 10:1, and a more preferred ratio is 2:1 to 4:1. A preferred rate of flow for the Fast Air is 0.5 to 20 cfm, and a more preferred rate of flow is 3 to 10 cfm. Cryogenic gases, such as the boil-off from liquid $N_2$, can be used to achieve subambient temperature programming down to -100° C.

The apparatus can also contain other regions which are maintained at a constant temperature. In particular, it may be desirable to thermostat the low pressure transducer, the high pressure transducer, and any of the gas conduits which are in fluid communication with the reactor. Such additional heated zones can increase the accuracy of adsorption and desorption measurements made by the volumetric method and can reduce the time to degas the apparatus.

A platform 210 supports a furnace or an insulated flask and provides means for the temperature controlled zone to be raised or lowered about a reactor. The platform is remotely raised and lowered using a pneumatic piston. This design enables very rapid switching between the use of a furnace and insulated flask for temperature control.

Electropneumatic valves 204 and 206 are attached to the Furnace Air Manifold to control the flow of cooling air to furnaces and to position the pneumatic platforms. The valves are remotely actuated. Valves are widely available for noncryogenic gases. An example of a preferred valve for the flow of a cryogenic gas is model SV-91 and is rated for service at −196° C.

A temperature controller is provided for each furnace. A preferred temperature controller is a microprocessor controlled unit, has proportional, integral, and derivative control, is multilevel programmable, and has dual outputs. Programmable control allows the temperature controller to change the temperature of a reactor at set rates. Dual control allows the temperature controller to simultaneously control both a heating current and cooling gas flow to a furnace, thus providing means for time programmable cooling. An example is model CN8622 made by Omega Engineering of Stamford, Conneticut. An alternative embodiment uses a temperature controller which is interfaced to a computer so as to be able to remotely controlled. An example is model CN2042 made by Omega Engineering.

The novel arrangement of vents and components downstream of the reactors provide an improved degree of flexibility in the apparatus. A separate vent for each reactor, the Bypass Valve, and the BPR is provided. Each vent includes a connector, which provides means to quickly connect tubing to a vent and thus direct the effluent to an analytical device or to alter the flow path. Separate vents and metering valves for each reactor provide means to individually control and measure the flow rate through each reactor when gas is simultaneously passing through more than one reactor. A separate vent for the BPR provides means for a BPR/Vent Selector 3-way valve to enable unexpectedly quick switching between gas flow at ambient and high pressure. Another improvement of the apparatus is that when operating at high pressure, added flexibility is achieved by not having the gas flow from a reactor directly enter the BPR, but is directed to the BPR Feed port. In the preferred embodiment, a short piece of SS tubing is used to shunt the BPR Feed port to the BPR In port. In an alternative embodiment, the shunt is replaced with other devices such as a cold trap to remove condensable substances from the gas flow or a gas sampling valve. In the latter example the sample effluent from the GSV is routed to the BPR In port. A preferred vent consists of a bulkhead union constructed of 316 SS.

The BPR 212 is an upstream pressure regulating device which isolates the pressure of gas upstream from it from atmospheric pressure, thereby allowing a reaction to be run at elevated pressures. Opening the BPR Pressurize Valve increases the setpoint of the BPR. The BPR Vent Valve allows the setpoint pressure in the BPR to be reduced down to 1 atm. A preferred BPR is of the dome loaded type, is constructed of type 316 SS with a VITON diaphragm, has an internal volume to which the reaction gas is exposed of <10 mL, and has a pressure rating of 1500 psia. An example is model 90 W manufactured by Grove Valve & Regulator Co. of Oakland, California. Alternative embodiments are a spring loaded BPR, a reverse acting mass flow controller such as manufactured by Brooks Instrument, Hatfield, PA, and a control valve such as manufactured by Badger Meter, Inc, of Tulsa, OK. Another alternative embodiment utilizes a remotely controlled upstream pressure regulating device. Automatic operation of a dome loaded BPR, reverse acting MFC, and control valve is readily achieved by those skilled in the art of gas flow. Both manually and remotely controlled upstream pressure regulating devices are available with a pressure rating of 10,000 psia.

The Vacuum System, FIG. 10, consists of those parts necessary to maintain and measure the vacuum. The Vacuum System evacuates gas from the Gas Manifold and displays the pressure of the Vacuum Manifold. The Vacuum System is depicted at FIG. 9, and a description follows.

The Vacuum Manifold consists of a piece of wide bore SS tubing to which various components are attached. A preferred Vacuum Manifold has an I.D. of about from ½ to 8" and has a volume of about 1 to 20 L. A more preferred Vacuum Manifold has an I.D. of about 2.5" to 6" and has a volume of about 3 to 10 L. The Vacuum Manifold deliberately has a large volume so as to substantially shorten the time necessary to rough evacuate the Reaction Manifold prior to evacuating in the high vacuum mode.

The bellows type Gas Manifold/Vacuum Manifold Valve separates the Gas Manifold from the Vacuum Manifold. Its presence substantially increases the accuracy of measurements of the adsorption and desorption of a solid with a gas made by the volumetric technique. This improvement obtains since the dosing volume no longer includes the volume of the Gas Manifold. The valves provide means to rough pump the Gas Manifold before opening it to the diffusion pump.

Vacuum Valve A 300 and Vacuum Valves B and C control the path of an evacuation and are remotely actuated. A preferred valve for Vacuum Valves A and C is of the bellows type as previously described. A preferred valve for Vacuum Valves B is similar except that the preferred range of tubulation size is about 0.5 to 1".

A preferred high vacuum gauge is an ionization gauge 302 with a pressure range of about $1\times10^{-2}$ to $1\times10^{-10}$ torr, and includes a digital readout of the pressure. The filament in an ionization gauge will burn out if exposed to pressures above about 0.01 torr. A preferred ionization gauge also includes circuitry to automatically turn off the gauge if the pressure is >0.01 torr. An example is model IG3 made by Inficon of East Syracuse, New York.

The Pirani gauge 304 is directly attached to the Vacuum Manifold. The gauge reads the pressure of the Vacuum Manifold in the range of about $1\times10^{-4}$ to 600 torr. In a preferred embodiment of the invention, this gauge is part of the circuitry to detect an over pressure error. If the pressure in the Vacuum Manifold exceeds about 0.1 torr, a circuit removes power from the diffusion pump to keep it from being damaged. A preferred Pirani gauge is constructed of SS. An example is the MODUCEL gauge made by MKS of Boulder, Colo.

The diffusion pump is directly attached to the Vacuum Manifold and evacuates it to a low pressure, achieving an ultimate vacuum of $10^{-9}$ torr. A preferred diffusion pump is constructed of SS, has a pumping speed of from 30 to 500 L/s, has an internal water cooled optically opaque baffle, and can achieve an ultimate vacuum of at least $10^{-8}$ torr. An alternative embodiment uses a turbomolecular pump.

The mechanical pump reduces the pressure in the Vacuum Manifold to a pressure low enough to enable the diffusion pump to work. A preferred mechanical pump is of the two stage design, can achieve an ultimate pressure of about $1 \times 10^{-3}$ torr, and has a pumping speed of about 25 to 200 L/S.

The Computer System provides means to calculate, display, store, print, and recall data. A wide choice of computer systems utilizing personal computers is readily available. The Computer System does not directly control any of the other systems in the preferred embodiment of the invention, but would interact with each of the other systems in an alternative embodiment of the invention which provides means for more automation. This is achieved by the addition of one or more circuit boards which provide means for A/D (analog to digital) conversion, D/A (digital to analog) conversion, digital I/O (input/output) signals, and timers. Also added are solid state relays to interface the output of the digital I/O board to electropneumatic control means, and additional software to enable all valves to be operated via the computer, and pressure, temperature, and flow to be controlled and measured by the computer. The required computer boards and software are readily available from a variety of vendors. An example is products of National Instruments of Austin, Tex.

The Analyzer System contains means to at least partially analyze the composition of the effluent from a reactor. The Analyzer System consists of (1) components necessary for the detector to be in fluid communication with the effluent of a reactor and (2) an analyzer which contains a detector in fluid communication with the reactor. The choice of analyzer, its placement in the apparatus, and the means of fluid communication depend on the particular measurement being made. The preferred Analyzer System for analysis of chemical reactions when neither adsorption nor desorption measurements are needed consists of (1) a gas sampling valve which is downstream from a vent so as to direct pulses of the reactor effluent a detector, and (2) a gas chromatograph analyzer.

The preferred Analyzer System for analysis of TPC measurements consists of (1) SS tubing connected to the downstream side of a vent so as to transport reactor effluent to a detector, and (2) a thermal conductivity detector. Alternative preferred analyzers for this Analyzer System is a flame ionization detector, an ultrasonic detector, a gas density balance, an ionization detector, and an infrared spectrometer. Each of these alternative analyzers are well known to those skilled in the art and are commercially available. A preferred Analyzer System for the analysis of the reactions of gases with solids and including analysis of TPC measurements consists of (1) a molecular leak downstream from a vent so as to provide a means to transport a small quantity of the reactor effluent to an evacuated chamber containing a detector, and (2) a mass spectrometer analyzer. The preferred analyzer for performing temperature programmed desorption by the direct evacuation method is a mass spectrometer detector inside of the Vacuum Manifold.

The apparatus is contained in an enclosure of novel design, here termed partial double wall construction. In this construction appropriate components are mounted on an interior panel which is self supporting, inside of the main outer wall, and the mounted components are accessible to a user of the apparatus. By way of illustration, consider the case of a single inlet valve. Using the method of partial double wall construction, the valve is mounted on a very small self supporting panel. This small panel is placed just inside of the outer wall which in turn has a small hole to provide access to the valve. By this means, the apparatus is normally completely protected by its enclosure, the entire wall can be removed so as to enable nearly complete access to the interior of the apparatus, and the functionality of the apparatus is totally unaffected by the complete removal of the wall.

The general method of utilizing the preferred embodiment has been described in reference to the more simplified version depicted in FIG. 2. In particular, the dosing volume used for measuring the amount of gas adsorbed on or desorbed from a solid sample utilizing the volumetric method is mainly the volume contained in the Reaction Manifold of FIG. 9. This volume is isolatable from and much smaller than the volume of the Gas Inlet Manifold of FIG. 8, thereby increasing the accuracy of the measurement. Additional methods are obvious to those skilled in the art based on the preceeding functional description.

The principles, preferred embodiments, and methods of operation of the present invention have been described in the preceding specification. These descriptions are not meant to delineate all possible specifications, configurations of components, variations of components, materials of construction, modes of operation, or features of the machine. Many permutations of these items are possible and other components can be added for the purpose of enabling other measurements while retaining the aforementioned novel multifunctional capabilities of the present invention. Variations and changes may be made by those skilled in the art without departing from the spirit of the present invention. In particular, there are many alternative choices of materials of construction for components which are in contact with reaction media, such as valves, tubing, and pressure transducers. In addition, there is a wide choice of packing materials and gaskets available for valves. Also, it has been noted that the pressure rating of the system can be increased to 3500 psi without any degradation in performance and maintaining the ability of full computer control. However, very few reactions are performed at pressures above 1500 psia. Pressures up to 10,000 psi can be achieved with the present invention, but at some loss in performance.

In order to give specific illustration of the nature of the invention and the manner of practicing it, the following working examples are described. However, it is to be fully understood that the invention is not limited to the specific measurements and details described in the examples.

In all of the following examples the apparatus is the preferred embodiment as described in connection with FIGS. 8 through 13, unless stated otherwise. More particularly, the Gas Inlet System accommodates eight different reaction gases which include $O_2$, $N_2$, CO, $H_2$, and He, and a mass flow controller controls the rate of flow of all reaction gases with the exception of $N_2$. A computer system was used for data analysis and to control the mass spectrometer.

EXAMPLE 1

A furnace was heated to 1000° C. and held at that temperature for >1 hr without the fan on so that the temperature of the internal parts of the furnace equilibrated. The temperature of the outer surface of the furnace was measured at the vertical midpoint of the furnace and at a point which is on the opposite side of the furnace from which the fan is located. The temperature was found to be 175° C., which is too hot to be easily handled. The fan was turned on and the temperature dropped to 85° C. With the Fast Air also on, the temperature dropped to 51° C. In another experiment, a furnace of 6" O.D. and having an annular air space adjacent to the outer shell was used. After equilibration of the furnace at 1000° C., the temperature of the shell was 120° C. An air flow reduced the temperature to 37° C. This Example shows the capability of the invention to use an external fan or internal air flow while heated to a high temperature to greatly lower the surface temperature of a furnace, thereby making it safer to use. This also allows the use of a furnace of much smaller diameter than expected and which therefore will have unusually fast thermal response.

EXAMPLE 2

The apparatus of Example 1 was used. A reactor of fused quartz was heated to 1100° C. The furnace was then automatically lowered and removed from the apparatus in 10 s. The reactor cooled to a temperature of 25° C. in 3 min. The furnace was reinstalled in 10 s. This Example demonstrates the ability of the invention to cool a reactor at an extremely fast rate.

EXAMPLE 3

The apparatus of Example 1 was used. A temperature controller was programmed to rapidly heat a furnace to 1000° C. A temperature of 1000° C. was achieved in 3.3 min with no overshoot, corresponding to a heating rate of 303° C./min. This Example demonstrates the ability of the invention to heat to very high temperatures at an extremely fast rate and with good temperature control. The heating rate of a furnace of the same size and design but utilizing a conventional ceramic support for the heating element heated at 70° C./min. This Example and Example 2 also demonstrate the need for both using an annular space with air flow at high temperatures and an ultra light inner insulation in order to achieve exceptionally fast thermal response.

EXAMPLE 4

A furnace identical to that of Example 1 was used. The furnace was programmed to heat to 1000° C. and held at that temperature for 1 hr so that the temperature of the internal parts of the furnace equilibrated. The temperature controller was then turned off and the rate of cooling of the furnace measured in the absence of internal cooling air. The interior of the furnace cooled to 500° C. in 14 min, to 100° C. in 80 min, and to 35° C. in 145 min. This experiment shows the rate of cooling of the furnace without flowing a cooling gas inside of the furnace is relatively slow. A similar experiment was done except that Fast Air was directed to the interior (not annular space) in the furnace. The flow of air was about ⅓ the maximum amount which can be conveniently used by the apparatus. The interior of the furnace cooled to 500° C. in 1 min, to 100° C. in 4 min, and to 28° C. in 10 min. After cooling to 411° C. the cooling air was briefly turned off and the temperature rose to 532° C., indicating that the cooling is much higher in the interior region of the furnace which is directly exposed to the air flow. This Example shows that the invention can give very fast cooling of the interior of a furnace if a flow of cooling gas is directed to the interior of the furnace. Faster rates of cooling are expected with the use of a higher gas flow or the use of a cryogenic gas.

EXAMPLE 5

The apparatus of Example 1 was used. A furnace was heated to 1000° C. and held at that temperature for at least 1 hr so that the temperature of the internal parts of the furnace equilibrated. The furnace was then turned off and a flow of cooling air was started through the annular space of the furnace. The flow of air was approximately ⅓ the maximum amount which can be conveniently used by the apparatus. The interior of the furnace cooled to 500° C. in 6 min, to 100° C. in 27 min, and to 35° C. in 45 min. In a similar experiment the cooling air was briefly turned off after the interior of the furnace had cooled to 501° C. The temperature only rose to 518° C., indicating that the entire furnace was being cooled nearly uniformly by the air flow. This Example demonstrates that the invention can give rapid cooling of a complete furnace. Faster rates of cooling are expected with the use of a higher gas flow or the use of a cryogenic gas.

EXAMPLE 6

The apparatus of Example 1 was used. The Fast Air cooling line for a furnace was connected to a tank of $CO_2$ with a delivery pressure of 20 psig. The flow of cooling gas was about 1/5 the maximum amount which can be conveniently used by the machine and neither the regulator on the gas tank nor the tubing between the tank and furnace were insulated. Consequently, the experiment was not optimized for maximum cooling nor were the operating parameters of the temperature controller optimized. The furnace cooled to a temperature of −40° C. In a similar experiment, a flow of $CO_2$ was used to cool a furnace to −18° C. The furnace was then programmed to heat to 500° C. at a rate of 20° C./min. For setpoint temperatures above 62° C., the actual temperature of the furnace was <1° C. different from the setpoint temperature, and at lower temperatures the difference was no more than several degrees. This Example shows that the invention can be used to achieve subambient temperatures and subambient temperature programming with good temperature control. Lower temperatures can be achieved by the use of a higher gas flow or the use of $N_2$ gas.

EXAMPLE 7

The apparatus of Example 1 was used. A furnace was programmed to heat from 24 to 74° C. at 10° C./min. The operating parameters of the temperature controller were not optimized. The results are shown in the following table as Run #1. In a similar run, the Fast Air cooling line was simultaneously controlled by output 2 of the temperature controller. The results are shown in the following table as Run #2. This Example shows that the invention can achieve improved temperature control during temperature programming by the use of a controlled flow of a gas into the annular space of a furnace.

TABLE 1

| Run # | Ideal T (°C.): | 24 | 34 | 44 | 54 | 64 | 74 |
|---|---|---|---|---|---|---|---|
| 1 | deviation (°C.): | 0 | +11 | +23 | +21 | +17 | +7 |
| 2 | deviation (°C.): | 0 | +6 | +7 | 0 | −2 | +3 |

EXAMPLE 8

The apparatus of Example 1 was used. The Vacuum Manifold was evacuated. A typical base pressure was $1 \times 10^{-8}$ torr, and the minimum pressure achieved was $6 \times 10^{-9}$ torr. A 0.47 g sample of gamma alumina was put inside of a glass reactor and heated to 500° C. in flowing $H_2$ at 1 atm. The reactor was then evacuated in the roughing mode. It took about 1 s for the pressure in the Reaction Manifold to drop to 2 torr, which is low enough to safely switch to the high vacuum mode of evacuation. Upon switching, the the pressure in the Vacuum Manifold remained well below $10^{-2}$ torr which is safe for the ionization gauge and it took 20 s for the pressure in the Vacuum Manifold to drop $1 \times 10^{-5}$ torr. This Example shows that the invention can achieve a very high vacuum and can pump down extremely fast.

EXAMPLE 9

The apparatus of Example 1 was used. The Gas Manifold, Reaction Manifold, and Low Pressure Transducer were evacuated and then isolated from the Vacuum Manifold. The total leak into the Gas Manifold, Reaction Manifold, and low pressure transducer was $2 \times 10^{-8}$ mL (STP)/s. In another experiment, the Gas Manifold, Reaction Manifold, and each of the eight lines for a reaction gas between the Gas Manifold and the redundant shutoff valves in the Gas Inlet System were pressurized to 1001 psia and then the redundant shutoff valves were closed. After 3 h there was no drop in pressure. This Example demonstrates that the invention can be constructed so as to have an extremely low leak level, both under high vacuum and at high pressure.

EXAMPLE 10

The apparatus of Example 1 was used. A 0.0295 g sample of 2.0% Co supported on gamma alumina was pretreated by heating to 1100° C. under vacuum. The surface area of the sample was determined in the conventional manner by measuring the adsorption of $N_2$ gas at 78K using the low pressure transducer to monitor the amount of adsorption. Data were entered into a computer program to calculate the results. An excellent BET plot resulted which yielded a surface area of 71.6 $m^2/g$ and a BET constant of 266. This Example demonstrates the ability of the invention to measure the surface area of a solid, to do so after pretreatment of a sample at very high temperature, and the ability to accurately measure the adsorption of a gas on a solid at very low temperature.

EXAMPLE 11

The apparatus of Example 1 was used. A 0.85 g sample of 0.05% Pd supported on gamma alumina was pretreated by heating to 450° C. in flowing $H_2$ followed by evacuation at this temperature. The dispersion of the catalyst was determined in the conventional manner by measuring the amount of $H_2$ chemisorption at 27° C. (defined as the difference in adsorption between two isotherms which are separated by evacuation of the sample at 27° C.). The dispersion of the sample was found to be 11.4%, corresponding to the chemisorption of 0.0051 mL (STP) of $H_2$. This Example demonstrates the ability of the invention to accurately measure the chemisorption of very small quantities of gas on a solid. The sensitivity of the apparatus for measuring the adsorption of a gas on a solid is found to be about 0.0002 mL STP, which is about 10-fold higher than any of the prior art devices.

EXAMPLE 12

The apparatus of Example 1 was used. A 0.501 g sample of 2% Co supported on gamma alumina was put in a SS reactor. A gas sampling valve was attached to a vent of the machine and plumbed so as to direct a sample of the reactor effluent to a gas chromatograph. The sample was pretreated by oxidation at 500° C. in a flow of $O_2$ and then reduction at 500° C. in a flow of $H_2$. A flow of CO and $H_2$ was then started through the reactor at 300° C. and a feed ratio of $H_2/CO=3$. The activity of the sample was determined for the hydrogenation of CO. The main product was found to be methane. The conversion was measured at pressures of 16, 150, 500, and 950 psia and at temperatures between 250° and 310° C. The activity of the catalyst declined during the measurements. Conventional analysis of the analytical data showed that the order of the reaction with respect to the total pressure was about 1.0 and the activation energy of the reaction was about 80 kJ/mol. This Example shows that the invention can be used to run a reaction at high pressures, and that the invention can be used to determine many reaction parameters such as the conversion, products, catalyst lifetime, activation energy, and order of reaction.

EXAMPLE 13

A Gas Manifold and Vacuum Manifold very similar to that of Example 1 was connected to a thermal conductivity detector (TCD) contained in a furnace equilibrated at about 50° C. by metal tubing. A flow of 5% $H_2$ in Ar (as could be used in a temperature programmed reduction experiment) was divided into two streams. One stream flowed through the reference side of the TCD and the other steam flowed through the Gas Manifold and then through the sample side of the TCD. The TCD was allowed to equilibrate (defined as the drift of the output voltage being reduced to 0.02 mV in 10 min). The TCD was then turned off for 9 min (the gas flow continued) and then turned back on. It took 4 min for the TCD to stabilize. Therefore, equilibration time in excess of 4 min, defined as excess equilibration time, would be due to having to equilibrate a gas mixture flowing through the TCD. In a second experiment, the TCD was allowed to equilibrate in a gas flow of 5% $H_2$ in Ar and then the gas lines were purged with a mixture of 5% $O_2$ in He (as could be used in a successive temperature programmed oxidation experiment). The mixture of 5% $H_2$ in Ar was again flowed through the system and the TCD turned back on. The excess equilibration time was 72 min, being the time it took the $H_2$/Ar mixture to completely flush the $O_2$/He mixture from the gas lines. In a similar experiment, the mixture of 5% $O_2$ in He was removed by brief evacuation. The mixture of 5% $H_2$ in Ar was then again flowed through the system and the TCD turned back on. It was found that the excess equilibration time was only 9 min. This Example demonstrates that the invention can be used to evacuate the gas lines going to a detector, thereby achieving a much faster equilibration time than when flushing the gas from the lines.

EXAMPLE 14

A Gas Manifold and Vacuum Manifold very similar to that of Example 1 was connected to a SS reactor and the exit of the reactor was connected with metal tubing to a leak valve of a mass spectrometer (MS). A 0.1 g sample of Rh-Zn supported on silica (4% Rh by weight, Rh/Zn atomic ratio=3.3) was placed in the reactor and pretreated by reduction in flowing $H_2$ at 400° C. followed by evacuation and then cooling to 25° C. The amount of CO chemisorption was measured in the conventional manner at 25° C. and found to be 0.062 mL STP. Following the chemisorption of CO, a 21 mL/min flow of He was passed through the reactor and the leak valve adjusted so as to give a pressure in the MS of $5 \times 10^{-6}$ torr. The reactor was then heated from 30° to 400° C. at 20° C./min and the evolution of CO was measured by monitoring mass 28 with the MS. This type of experiment is termed temperature programmed desorption. The CO desorbed in a single peak with a peak height of $9.6 \times 10^{-8}$ A. The leak valve was then removed from the MS and the reactor was attached to the vacuum system of the MS using $\frac{1}{4}''$ O.D. metal tubing. The catalyst was then pretreated as before and the CO chemisorption repeated, yielding the same result. A temperature programmed desorption experiment was now performed in which the desorbing CO was directly evacuated into the MS. The CO desorbed in a single peak with a peak maximum of $1.48 \times 10^{-5}$ A. This Example shows that the invention can be used to do temperature programmed desorption experiments with MS analysis in both the conventional mode in which the desorbing gas is swept out of the reactor by a carrier gas and is then bled into a MS as well as by an improved method involving direct evacuation into a MS. Further, the latter method yields about a 150-fold increase in sensitivity.

EXAMPLE 15

The apparatus of Example 1 was used. A temperature programmed desorption experiment was done with a sample of 2% Ru supported on alumina. The sample was exposed to a mixture of $CO+H_2$ at 25° C., the reactor evacuated, and then a 20 mL/min flow of He was passed through the reactor and to a leak valve attached to a MS. The furnace was cooled with $CO_2$ and then the temperature was ramped from $-18°$ to 500° C. at 20 C./min. The desorption of $H_2$, CO, and $CH_4$ (formed by reaction between the first two gases) was measured by monitoring masses 2, 28, and 16, respectively, using a mass spectrometer. A large and broad CO peak was observed, but only very small amounts of $H_2$ and $CH_4$ were observed. This Example shows that the invention can can be used to do subambient temperature programmed desorption.

EXAMPLE 16

The apparatus of Example 1 was used. A 0.1007 g sample of 2% Mo supported on alumina was placed into a reactor of fused quartz. The sample was pretreated by oxidation at 600° C. in flowing $O_2$ followed by evacuation and then cooling to 25° C. This pretreatment converts the sample to $MoO_3$ supported on alumina. The vent of the reactor was attached to the sample side of a thermal conductivity detector (TCD). A 24 mL/min flow of 5% $H_2$ in Ar was then passed through the reference side of the TCD and a similar flow was passed through the reactor and then through the sample side of the TCD. The temperature of the furnace was then raised from 60° to 1200° C. at the rate of 20° C./min while the output of the TCD was monitored. When the $MoO_3$ gets reduced, $H_2$ is consumed from the flow of carrier gas and a peak is observed. This type of experiment is termed temperature programmed reduction. A small peak was observed near 580° C. and a large peak was observed near 950° C., corresponding to the reduction of $MoO_3$ to Mo metal. This Example shows that the invention can be used to do temperature programmed reduction experiments and can do them to unusually high temperatures.

What is claimed:

1. A laboratory apparatus for accurately measuring the amount of gas adsorbed on or desorbed from a solid by a volumetric method, comprising; a combination of a first valve and variable conductance valve to receive gas from a gas supply;

reacting means downstream from and in fluid communication with said combination of said first valve and said variable conductance valve, for reacting a solid sample with said gas from said gas supply received via said combination of said first valve and said variable conductance valve;

vacuum means comprising a vacuum pump with a rated ultimate vacuum of less than about 0.01 torr and operable to evacuate said reacting means and being downstream from and in fluid communication with said combination of said first valve and said variable conductance valve and being upstream from said reacting means; a second valve means downstream from and in fluid communication with the combination of said first valve and said variable conductance valve and operable to isolate said vacuum means from said reacting means;

a third valve means downstream from said reacting means and operable to cut off gas emanating from said reacting means;

pressure controlling means operable to control the pressure of said reacting means to a maximum pressure of at least one atmosphere and less than 10,000 psia, said pressure controlling means being downstream from said third valve means and in fluid communication therewith and operable to receive gas therefrom and to discharge gas emanating from said third valve; means a fourth valve means operable to isolate said reacting means from gas emanating from said combination of said first valve and said variable conductance valve;

high pressure measuring means operable to measure the pressure of a gas at pressures above one atmosphere, said high pressure measuring means being downstream from and in fluid communication with said combination of said first valve and said variable conductance valve and being upstream from and in fluid communication with said pressure controlling means; low pressure measuring means operable to measure the pressure of a gas at pressures substantially below 1 atm and having an accuracy of at least 0.5% of full scale and operable to measure a pressure of 400 torr with an error of less than about 5 torr, said low pressure measuring means being downstream from and in fluid communication with said combination of said first valve and said variable conductance valve and being upstream from and in fluid communication with said fourth valve means;

a fifth valve means upstream of said low pressure measuring means, operable to isolate the low pressure measuring means from gas emanating from the said combination of said first valve and said variable conductance valve;

heat transfer means operable to add or remove heat from said reacting means; temperature controlling means operable to control the temperature of said heat transfer means.

2. The apparatus according to claim 1 and further comprising;

gas analyzer means downstream from and in fluid communication with said third valve means and operable to measure at least one parameter of said gas and to discharge said gas emanating from said third valve means;

and wherein said temperature controlling means is operable to vary temperature with respect to time in a predetermined manner.

3. A laboratory apparatus for performing temperature programmed characterization at pressures near 1 atm, comprising;

a combination of a first valve and variable conductance valve receiving gas from a gas supply;

reacting means downstream from and in fluid communication with said combination of said first valve and said variable conductance valve, for reacting a solid sample with said gas from said gas supply received via said combination of said first valve and said variable conductance valve;

vacuum means comprising a vacuum pump with a rated ultimate vacuum of less than about 0.01 torr and operable to evacuate said reacting means said vacuum means being downstream from and in fluid communication with said combination of said first valve and said variable conductance valve and in fluid communication with said reacting means;

a second valve means downstream from and in fluid communication with the combination of said first valve and said variable conductance valve and operable to isolate said vacuum means from said reacting means;

a third valve means downstream from said reacting means and operable to cut off gas emanating from said reacting means;

gas analyzer means downstream from and in fluid communication with, said third valve means and operable to measure at least one parameter of said gas and to discharge said gas emanating from said third valve means;

heat transfer means operable to add or remove from said reacting means; and temperature controlling means operable to control the temperature of said heat transfer means and operable to vary temperature control with respect to time in predetermined manner.

4. The apparatus of claim 3 comprising;

a fourth valve means operable to isolate said reacting means from gas emanating from said combination of said first valve and said variable conductance valve;

low pressure measuring means operable to measure the pressure of a gas at pressures substantially below 1 atm and having an accuracy of at least 0.5% maximum error of full scale and operable to measure a pressure of 400 torr with an error of less than 5 torr, said measuring means being downstream from and in fluid communication with said combination of said first valve and said variable conductance valve and being upstream from and in fluid communication with said fourth valve;

a fifth valve means upstream of said low pressure measuring means operable to isolate the low pressure measuring means from gas emanating from the said combination of said first valve and said variable conductance valve.

5. The apparatus of claim 3 further comprising;

high pressure measuring means operable to measure the pressure of a gas at pressures above 1 atm, said measuring means being downstream from and in fluid communication with said combination of said first valve and said variable conductance valve and being upstream from and in fluid communication with said pressure controlling means; pressure controlling means operable to control the pressure of said reacting means to a maximum pressure of at least 1 atm and less than 10,000 psia and being downstream from said third valve means said pressure controlling means operable to discharge gas emanating from said third valve means.

6. A laboratory apparatus for performing temperature programmed characterization at pressures near 1-atm, comprising;

a combination of a first valve and variable conductance valve to receive gas from a gas supply;

reacting means downstream from and in fluid communication with said combination of said first valve and said variable conductance valve, for reacting a solid sample with said gas from said gas supply received via said combination of said first valve and said variable conductance valve;

pressure measuring means operable to measure the pressure of a gas at pressures above 1 atm, said pressure measuring means being downstream from and in fluid communication with said combination of said first valve and said variable conductance valve and being upstream from and in fluid communication with said pressure controlling means;

heat transfer means operable to add or remove heat from said reacting means; temperature controlling means operable to control the temperature of said reacting means and operable to vary temperature with respect to time in a predetermined manner;

pressure controlling means operable to control the pressure of said reacting means to a maximum pressure of at least 1 atm and less than 10,000 psia and being downstream from said reacting means and in fluid communication therewith and receiving gas therefrom, said pressure controlling means operable to discharge gas emanating from said reacting means;

gas analyzer means downstream from and in fluid communication with said reacting means and operable to measure at least one parameter of said gas and to discharge said gas emanating from said reacting means.

7. A laboratory apparatus for performing temperature programmed desorption, comprising;

a combination of a first valve and variable conductance valve to receive gas from a gas supply;

reacting means downstream from and in fluid communication with said combination of said first valve and said variable conductance valve, for reacting a solid sample with said gas from said gas supply received via said combination of said first valve and said variable conductance valve;

vacuum means comprising a vacuum pump selected from the group consisting of turbomolecular pump, diffusion pump, and a pump with rated ultimate vacuum of less than about $2 \times 10^{-6}$ torr, and operable to evacuate said reacting means, and being downstream from and in fluid communication with said combination of said first valve and said variable conductance valve and being upstream from said reacting means;

a second valve means downstream from and in fluid communication with the combination of said first valve and said variable conductance valve and operable to isolate said vacuum means from said reacting means;

a third valve means downstream from said reacting means and operable to cut off gas emanating from said reacting means;

an evacuable chamber downstream of said second valve means and upstream of said vacuum means;

a mass spectrometer probe in said evacuable chamber and operable to analyze at least one parameter of the gas in said evacuable chamber;

heat transfer means operable to permit heat transfer with said reacting means; and temperature controlling means operable to control the temperature of said heat transfer means and operable to vary temperature control with respect to time in a predetermined manner.

8. Apparatus according to any one of claims 1 through 7, wherein said heat transfer means is a furnace having an outer surface, and further comprising a fan means rated at at least 20 cubic feet per minute;

said fan means operable to direct a flow of air to the outer surface of said furnace and operable to cool the outer surface of said furnace.

9. Apparatus according to any one of claims 1 through 7 wherein said heat transfer means comprises a furnace, said furnace comprising a heating element;
said heating element of approximately cylindrical shape;
said heating element comprising an inner surface, heater means and thermal insulation having an outer surface;
said thermal insulation consisting of vacuum cast ceramic fiber;
said heater means adjacent to the inner surface of said heating element and spaced from the outer surface of said thermal insulation;
said heating element impervious to the flow of gas in a radial direction;
said furnace further comprising an outer shell;
at least one open annular space between said heating element and said outer shell;
at least one opening for a flow of gas to enter said annular space and at least one opening for said gas to leave said annular space;
controlling means operable to cause said gas to flow into said annular space to cool said outer shell while said heat transfer means is supplying heat to said reacting means;
and said controlling means operable to control by the means selected from the group consisting of manual means and computer means.

10. Apparatus according to any one of claims 1 through 7, wherein said heat transfer means comprises a furnace and cooling means; said cooling means selected from the group consisting of a cryogenic fluid contained in an insulated flask and a cryogenic gas;
said heat transfer means and said temperature controlling means acting in cooperation with each other to control the temperature of said reacting means in the range of about $-196°$ C. to less than about $1650°$ C.

11. An apparatus according to any one of claims 1 through 7, wherein said heat transfer means comprises a furnace and an insulated flask containing a cryogenic fluid;
raising and lowering means operable to raise and lower said heat transfer means about said reacting means; said raising and lowering means operable to be actuated by actuating means selected from the group consisting of manual actuation means, and computer controlled actuation means.

12. An apparatus according to any one of claims 1 through 7, wherein said temperature controlling means is a microprocessor controlled temperature controller with dual outputs operable to simultaneously control the heating and cooling of a furnace.

13. An apparatus according to any one of claims 1 through 7, wherein said heat transfer means comprises a furnace operable to heat at a maximum rate of at least $80°$ C./min and less than about $300°$ C./min.

14. An apparatus according to any one of claims 1 through 7, wherein at least one valve is remotely actuated and said apparatus further comprises computer means operable to control the extent of opening and closing of said at least one valve.

15. An apparatus according to any one of claims 1 through 7, further comprising a gas inlet manifold having at least one valve operable to isolate said gas inlet manifold from said gas source, and at least one value operable to isolate said gas source from said gas inlet manifold valve.

16. An apparatus according to any one of claims 1 through 7, wherein said reacting means comprises a removable reactor and a reactor harness;
said reactor harness connected to said removable reactor and having inlet and exit portions;
tubing connected to said inlet and exit portions;
said tubing having at least one internal filter having a surface area of at least 0.2 squ. in. and having a porosity of from 1 to 100 microns;
said filter to trap particulate matter in said tubing;
said reactor harness having a total volume of less than about 15 ml.

17. An apparatus according to any one of claims 1 through 7, and further comprising an enclosure containing said apparatus and having at least one outer wall;
said enclosure having at least one panel which is self supporting and adjacent to said outer wall and approximately parallel thereto and of substantially smaller surface area than said outer wall;
said apparatus having mounted on said panel;
an aperture in said outer wall enabling access to said mounted fitting or valve; said outer wall adapted to be easily removable from said enclosure without interfering with the operation of said apparatus.

18. An apparatus according to any one of claims 1 through 7, wherein said reacting means comprises a glass reactor;
said glass reactor having an entrance and exit ports;
said ports terminated with glass-to-metal seals having a glass tube end and a metal end; wherein said metal end of said glass-to-metal seals is held rigidly in a bracket.

19. An apparatus according to any one of claims 1 through 7, and further comprising at least one gas sampling valve in fluid communication with and upstream of said reacting means;

means for directing the flow of a gas into said gas sampling valve;

wherein said directing means is operable to permit pulses of said gas to flow through said reacting means.

20. An apparatus according to any one of claims 1, 2, 5, and 6, wherein said variable conductance valve comprises a valve selected from the group consisting of a metering valve and a mass flow controller wherein a setpoint of said controller is set manually or by computer control;

and said pressure controlling means is selected from the group consisting of a back pressure regulator wherein a setpoint is set manually or by computer control, a reverse acting mass flow controller wherein a setpoint is set manually or by computer control, and a variable conductance control valve wherein a setpoint is set manually or by computer control.

21. An apparatus according to any one of claims 1 and 2, wherein said variable conductance valve comprises a valve selected from the group consisting of a metering valve and a mass flow controller wherein a setpoint of said controller is set manually or by computer control;

said pressure controlling means is selected from the group consisting of a back pressure regulator wherein a setpoint is set manually or by computer control, a reverse acting mass flow controller wherein a setpoint is set manually or by computer control, and a variable conductance control valve wherein a setpoint is set manually or by computer control;

said heat transfer means comprises a furnace and cooling means;

said cooling means selected from the group comprising a cryogenic fluid contained in an insulated flask and a cryogenic gas;

said heat transfer means and said temperature controlling means acts cooperatively to control the temperature of said reacting means in the range of $-196°$ C. to a maximum temperature of at least $600°$ C.;

said pressure measuring means has an accuracy of at least 0.1% maximum error of full scale and is operable to measure a pressure of 400 torr with an error of less than 1.4 torr; and said vacuum means comprising a high vacuum pump selected from the group consisting of turbomolecular pump, diffusion pump, and pump with rated ultimate vacuum of less than about $2 \times 10^{-6}$ torr.

22. The apparatus of claim 21, wherein said pressure controlling means is operable to control the pressure of said reacting means to a maximum pressure of at least 200 psia.

23. The apparatus of claim 21, wherein said pressure controlling means is operable to control the pressure of said reacting means to a maximum pressure of at least 1000 psia.

24. The apparatus of claim 4, wherein said variable conductance valve comprises a valve selected from the group consisting of a metering valve and a mass flow controller wherein the setpoint of said controller is set manually or by computer control;

said heat transfer means comprises a furnace and cooling means; said cooling means selected from the group comprising a cryogenic fluid contained in an insulated flask and a cryogenic gas;

said heat transfer means and said temperature controlling means acting in cooperation with each other to control the temperature of said reacting means in the range of $-196°$ C. to a maximum temperature of at least $600°$ C.;

said pressure measuring means has an accuracy of at least 0.1% maximum error of full scale and is operable to measure a pressure of 400 torr with an error of less than 1.4 torr; and said vacuum means comprises a vacuum pump selected from the group consisting of a turbomolecular pump, a diffusion pump, and a pump with rated ultimate vacuum of less than about $2 \times 10^{-6}$ torr.

25. The apparatus of claim 9 wherein said controlling means is automatically operable to control the rate of flow of gas into said annular space so as to enable the temperature of said furnace to be decreased at a predetermined rate.

26. The apparatus of claim 25 wherein said gas is a cryogenic gas capable of cooling said furnace to a minimum temperature of at least below about $-20°$ C.

27. An apparatus according to any one of claims 2 through 5, further comprising a valve means downstream of and in fluid communication with said gas analyzer and operable to isolate said gas analyzer from said vent.

28. An apparatus according to any one of claims 1, 2, and 4, wherein said low pressure measuring means has an accuracy of at least 0.1% maximum error of full scale and is operable to measure a pressure of 400 torr with an error of less than 1.4 torr.

29. An apparatus according to any one of claims 1 through 5, wherein said vacuum means comprises a vacuum pump selected from the group consisting of a turbomolecular pump, a diffusion pump, and a pump with rated ultimate vacuum of less than about $2 \times 10^{-6}$ torr.

30. An apparatus according to any one of claims 1 through 5 and claim 7, wherein at least one of said valves is plumbed in a backwards orientation.

31. An apparatus according to any one of claims 1, 2 and 4 and further comprising gas inlet manifold means for allowing the entry of two or more gases into the apparatus;

and a valve member means operable to isolate said gas inlet manifold from said reaction means.

32. An apparatus according to any one of claims 1 through 5 and claim 7, wherein said vacuum means comprises a mechanical pump, a vacuum pump with rated ultimate vacuum of less than about $2 \times 10^{-6}$ torr, a vacuum measuring gauge, and a ballast volume of size greater than 1 L in fluid communication with said vacuum pump;

and said ballast volume operable to limit the pressure near the inlet of said high vacuum pump to a value below 0.01 torr when evacuation of said reacting means is switched at a pressure of said reacting means of roughly 1 torr from the roughing mode to the vacuum mode.

33. An apparatus according to any one of claims 1, 2, 5, and 6, wherein said reacting means comprises one or more reactors and flow directing means operable to direct the flow of gases through said reactors simultaneously;

at least one reactor having a selector valve downstream of and operable to receive gas exiting only from said at least one reactor;

each selector valve means having an independent vent;

said selector valve means operable to route effluent to said vent at ambient pressure and alternatively operable to route said effluent to said pressure controlling means.

34. An apparatus according to any one of claims 2 through 6, and further comprising at least one gas sampling valve means operable to be in fluid communication with and downstream of said reacting means;

flow means directing for the flow of a gas into said gas sampling valve means;

said gas analyzer means comprising a detector selected from the group consisting of a thermal conductivity detector, flame ionization detector, mass spectrometer, infrared spectrometer, gas density detector, ultrasonic detector, and a gas chromatograph; and said directing means operable to permit pulses of the reacting means effluent to be directed to said analyzer.

35. An apparatus according to any one of claims 1, 2, and 4, and further comprising a secondary path to said vacuum means; said secondary path comprising a valve in fluid communication with said vacuum means and in fluid communication with said combination of said first valve and said variable conductance valve and operable to isolate said vacuum means from said reacting means; said secondary path having fluid conductance low enough to enable pressure in the apparatus downstream of said first valve and upstream of said fourth valve means to be reduced.

36. An apparatus according to any one of claims 1, 2, and 4, and further comprising a evacuable chamber of volume less than 10 mL;

and a sixth valve means downstream from and in fluid communication with the combination of said first valve and said variable conductance valve and operable to isolate said evacuable chamber from said reacting means;

and said evacuable chamber operable to permit a dose of an accurately known amount of gas to be expanded into said reacting means.

37. An apparatus according to any one of claims 1, 2 and 4, wherein said reacting means comprises a reactor containing a solid sample; and at least one removable insert; said insert comprising a glass tube having two ends and an outer surface, said glass tube sealed at both ends and impervious to the flow of gas through said outer surface; said insert placed inside of said reactor thereby reducing the amount of volume of said reactor which is accessible to a gas.

38. An apparatus according to any one of claims 1 through 7, and further comprising a circulating pump;

said circulating pump having an inlet and exit portions;

tubing connected to said inlet and exit portions; said tubing in fluid communication with said reacting means; and said circulating pump in fluid communication with said reacting means thereby permitting a continuous flow of gas through said reacting means in a closed loop.

39. An apparatus according to any one of claims 1 and 2, and further comprising a secondary vacuum means downstream from and in fluid communication with and operable to evacuate gas emanating from said pressure controlling means, and wherein said low pressure measuring means comprising a pressure transducer with an electrical output;

and said pressure controlling means and said secondary vacuum means and the output of said pressure transducer control gas flow through said reaction means at pressures below 1 atm.

40. A process for measuring chemical reactions comprising:

providing an apparatus according to any of claims 1 through 7;

directing a gas to a reactor selected from the group consisting of a batch reactor, a tubular reactor, a fluidized bed reactor, a continuous stirred tank reactor, a slurry reactor, and a stirred autoclave reactor.

* * * * *